(12) United States Patent
Qi et al.

(10) Patent No.: US 9,427,523 B2
(45) Date of Patent: Aug. 30, 2016

(54) INFUSION PUMP SYSTEM AND METHOD

(71) Applicant: Bigfoot Biomedical, Inc., Milpitas, CA (US)

(72) Inventors: Wenkang Qi, Cupertino, CA (US); David Thrower, San Jose, CA (US); Tracy Brewer, Hayward, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 807 days.

(21) Appl. No.: 13/709,296

(22) Filed: Dec. 10, 2012

(65) Prior Publication Data

US 2014/0163462 A1    Jun. 12, 2014

(51) Int. Cl.
*A61M 5/172* (2006.01)
*A61M 5/145* (2006.01)
*A61M 5/168* (2006.01)

(52) U.S. Cl.
CPC .......... *A61M 5/172* (2013.01); *A61M 5/14566* (2013.01); *A61M 5/16831* (2013.01); *A61M 2205/14* (2013.01); *A61M 2205/33* (2013.01)

(58) Field of Classification Search
CPC .................. A61M 2205/581; A61M 5/14244; A61M 2205/582; A61M 5/172; A61M 2205/14; A61M 2205/18; A61M 5/16831
See application file for complete search history.

(56) References Cited

U.S. PATENT DOCUMENTS

| | | | |
|---|---|---|---|
| 6,126,595 A | 10/2000 | Amano | |
| 6,233,471 B1 | 5/2001 | Berner et al. | |
| 6,461,331 B1 | 10/2002 | Van Antwerp | |
| 6,474,219 B2 | 11/2002 | Kitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Kitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

*Asante Pearl Insulin Pump User Manual.* Sunnyvale, CA, Asante Solutions, Inc., Nov. 2012, 180 pages.

(Continued)

*Primary Examiner* — Aarti B Berdichevsky
(74) *Attorney, Agent, or Firm* — Fish & Richardson P.C.

(57) ABSTRACT

Some embodiments of an infusion pump system may be configured to detect when at least one component of the pump system is exposed to an impact above a threshold level. In particular embodiments, the infusion pump system can be equipped with a drive system detection system configured to detect when one or more components of the drive system are damaged or inoperable.

20 Claims, 12 Drawing Sheets

(56) References Cited

U.S. PATENT DOCUMENTS

| | | |
|---|---|---|
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Kitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman IV et al. |
| 6,960,192 B1 | 11/2005 | Flaherty et al. |
| 6,979,326 B2 | 12/2005 | Mann et al. |
| 6,997,911 B2 | 2/2006 | Kitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann |
| 7,029,455 B2 | 4/2006 | Flaherty |
| 7,033,338 B2 * | 4/2006 | Vilks ............... A61M 5/14244 604/152 |
| 7,054,836 B2 | 5/2006 | Christensen et al. |
| 7,104,972 B2 | 9/2006 | Møller et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,833,196 B2 * | 11/2010 | Estes ............... A61M 5/14244 362/101 |
| 8,211,062 B2 | 7/2012 | Estes et al. |
| 8,287,514 B2 | 10/2012 | Miller et al. |
| 8,454,557 B1 * | 6/2013 | Qi ............... A61M 5/172 604/151 |
| 8,945,044 B2 * | 2/2015 | Qi ............... A61M 5/172 604/67 |
| 2001/0056262 A1 | 12/2001 | Cabiri |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Kitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Malave et al. |
| 2005/0222645 A1 | 10/2005 | Malave et al. |
| 2005/0234404 A1 * | 10/2005 | Vilks ............... A61M 5/14244 604/151 |
| 2005/0238507 A1 | 10/2005 | Dilanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0178633 A1 | 8/2006 | Garibotto et al. |
| 2006/0184119 A1 | 8/2006 | Remde et al. |
| 2006/0200073 A1 | 9/2006 | Radmer et al. |

(56) References Cited

U.S. PATENT DOCUMENTS

| | | |
|---|---|---|
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0124002 A1 | 5/2007 | Estes et al. |
| 2007/0149926 A1 | 6/2007 | Moberg et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2008/0125700 A1 | 5/2008 | Moberg et al. |
| 2008/0172027 A1 | 7/2008 | Blomquist |
| 2008/0294109 A1* | 11/2008 | Estes ................. A61M 5/14244 604/141 |
| 2008/0306444 A1 | 12/2008 | Brister |
| 2010/0094251 A1 | 4/2010 | Estes |

FOREIGN PATENT DOCUMENTS

| | | |
|---|---|---|
| DE | 102 36 669 | 2/2004 |
| DE | 20 2005 012 358 | 10/2005 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/093648 | 11/2004 |
| WO | WO 2004/110526 | 12/2004 |
| WO | WO 2005/002652 | 1/2005 |
| WO | WO 2005/039673 | 5/2005 |
| WO | WO 2005/072794 | 8/2005 |
| WO | WO 2005/072795 | 8/2005 |
| WO | WO 2006/075016 | 7/2006 |
| WO | WO 2006/105792 | 10/2006 |
| WO | WO 2006/105793 | 10/2006 |
| WO | WO 2006/105794 | 10/2006 |
| WO | WO 2006/115913 | 11/2006 |
| WO | WO 2014/015239 | 1/2014 |

OTHER PUBLICATIONS

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

Patent Abstracts of Japan, vol. 1999, No. 04, and JP 11 010036 , Apr. 30, 1999 and Jan. 19, 1999, Toray Ind. Inc.

International Search Report and Written Opinion in International Application No. PCT/US2013/073883, mailed Mar. 21, 2014, 20 pages.

Supplemental European Search Report in Application No. EP 13862133, dated Jul. 4, 2016, 4 pages.

* cited by examiner

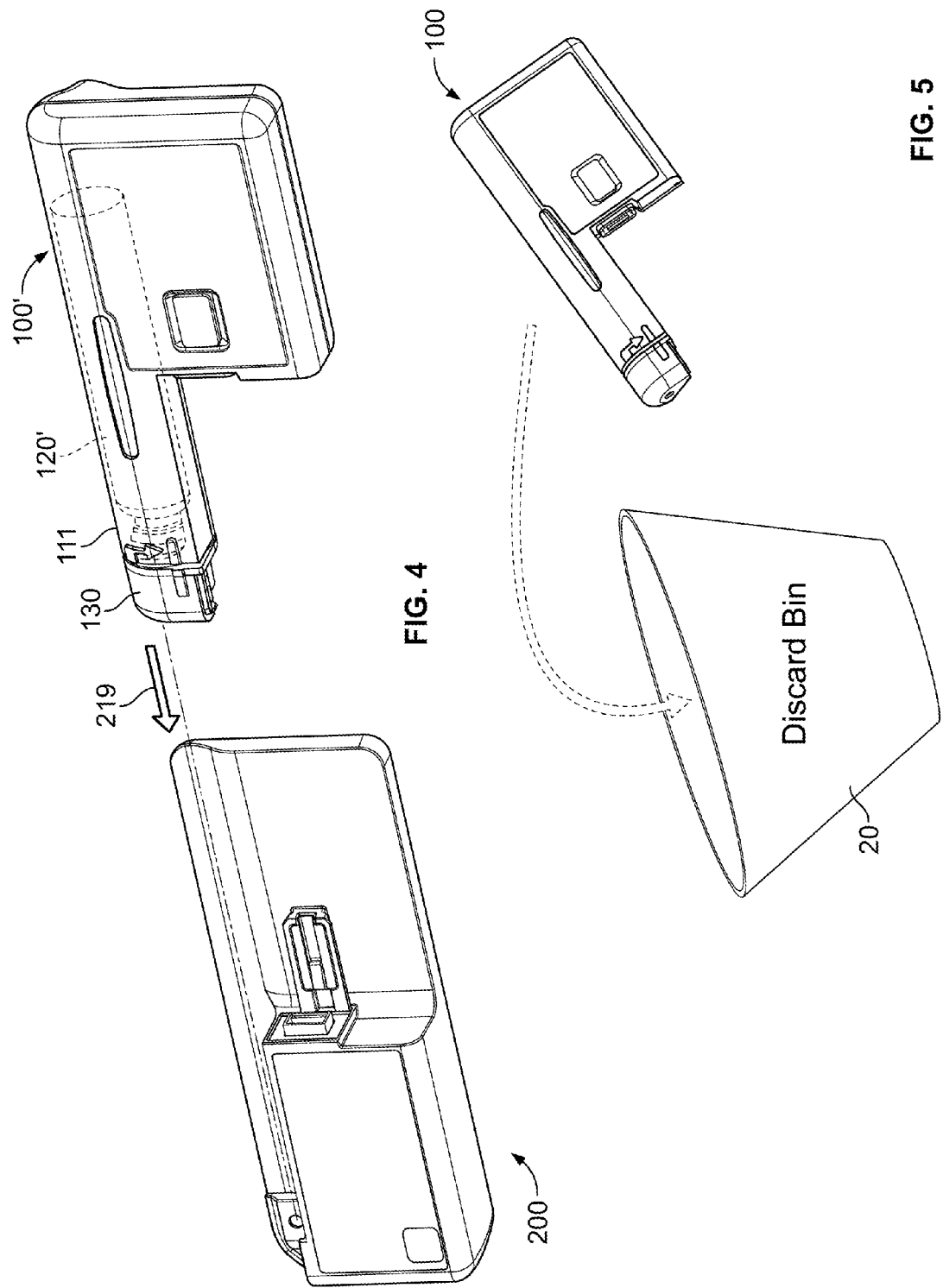

INFUSION PUMP SYSTEM AND METHOD

TECHNICAL FIELD

This document relates to an infusion pump system, such as a portable infusion pump system for dispensing a medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often need to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

In some circumstances, the ability of an infusion pump to deliver an accurately controlled dosage can be negatively affected if the pump device has sustained damage from a physical impact. Damage to an infusion pump device may result, for example, from dropping the infusion pump device onto a floor or other hard surface in a manner that could damage or otherwise hinder the drive system of the pump device.

SUMMARY

Some embodiments of an infusion pump system may be equipped with a drive system detection system configured to detect when one or more components of the drive system are damaged or inoperable. For example, the drive system detector can sense when an impact (or other event) has occurred to the drive system of the pump device, which thereby enables the infusion pump system to initiate appropriate patient safety countermeasures. Appropriate patient safety counter measures can include, for example, disablement of medicine delivery by the pump device, emitting an alarm to the user, and prompting the user to perform a number of remedial actions. In embodiments in which the pump device is a single-use disposable component and the pump controller is a reusable component, the drive system detector can be located in the pump device. Such a configuration can be useful because a significant impact imparted to the pump device component prior to connection (e.g., via a wired or wireless connection) with the controller component can be detected by the pump device component and identified by the controller component when the pump device component and controller component are initially connected. In such circumstances, the infusion pump system can initiate appropriate patient safety countermeasures prior to the patient's use of the system. If no such prior impact occurred, the system can be used in the normal fashion, and the drive system detector can continue to monitor for impacts above the threshold level while the pump device component and controller component are connected together. If such an impact is detected by the drive system detector while the pump device component and controller component are connected together, the infusion pump system can respond at that time by initiating appropriate patient safety countermeasures.

Particular embodiments described herein include a portable infusion pump system. The system may include a pump device including a pump housing that defines a space to receive a medicine, a drive system positioned in the pump housing to dispense the medicine from the pump device when the medicine is received in the space of the pump housing. The pump housing may house at least one electrically conductive element of a drive system detector, which optionally, is mounted to a component of the drive system. The system may also include a controller device removably attachable to the pump housing so as to electrically connect with the pump device. The controller device may house control circuitry configured to communicate with the drive system positioned in the pump housing to control dispensation of the medicine from the pump device. The control circuitry of the controller device can be configured to disable the pump drive system in response to the drive system detector indicating damage to one or more components of the drive system.

Some embodiments of a medical infusion pump system include a portable housing defining a space to receive a medicine, and a pump drive system to dispense medicine from the portable housing when the medicine is received in the space. The system may also include control circuitry that electrically communicates with the pump drive system to control dispensation of the medicine from the portable housing when the medicine is received in the space. The system may further include a drive system detector comprising at least one electrically conductive element coupled to a component of the pump drive system. The control circuitry may disable the pump drive system in response to the drive system detector indicating damage to one or more components of the drive system.

Other embodiments described herein include a method of controlling a portable infusion pump system. The method may include sensing that a drive system of a portable infusion pump system is damaged via a drive system detector including an electrically conductive element of that is coupled to a component of the drive system in the portable infusion pump system. The method may further include, in response to the sensing that the drive system detector indicates said drive system is damaged, disabling the pump drive system housed in the portable infusion pump system.

Some or all of the embodiments described herein may provide one or more of the following advantages. First, some embodiments of the infusion pump system may be configured to detect when one or more components of a pump drive system have sustained an impact that could potentially damage the system or otherwise cause over-dosage or under-dosage of medicine to the user. Second, some embodiments of the infusion pump system may initiate user safety countermeasures upon detection that the system has sustained an impact above a threshold level. Third, certain embodiments of an infusion pump system may prevent use of a damaged system that may have some potential for delivery of an improper medicine dosage if used. Fourth, some embodiments of the infusion pump system may include drive system detector located in the single use pump device thereby providing passive user safety protection. Fifth, the infusion pump system may be configured to be portable, wearable, and (in some circumstances) concealable. For example, a user can conveniently wear the infusion pump system on the user's skin under clothing or can carry the pump system in the user's pocket (or other portable location) while receiving the medicine dispensed from the pump device.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4-5 are perspective views of the pump device of FIGS. 1-2 being discarded and the controller device of FIGS. 1-2 being reused with a new pump device.

Like reference symbols in the various drawings indicate like elements.

DETAILED DESCRIPTION OF ILLUSTRATIVE EMBODIMENTS

Figure 1:
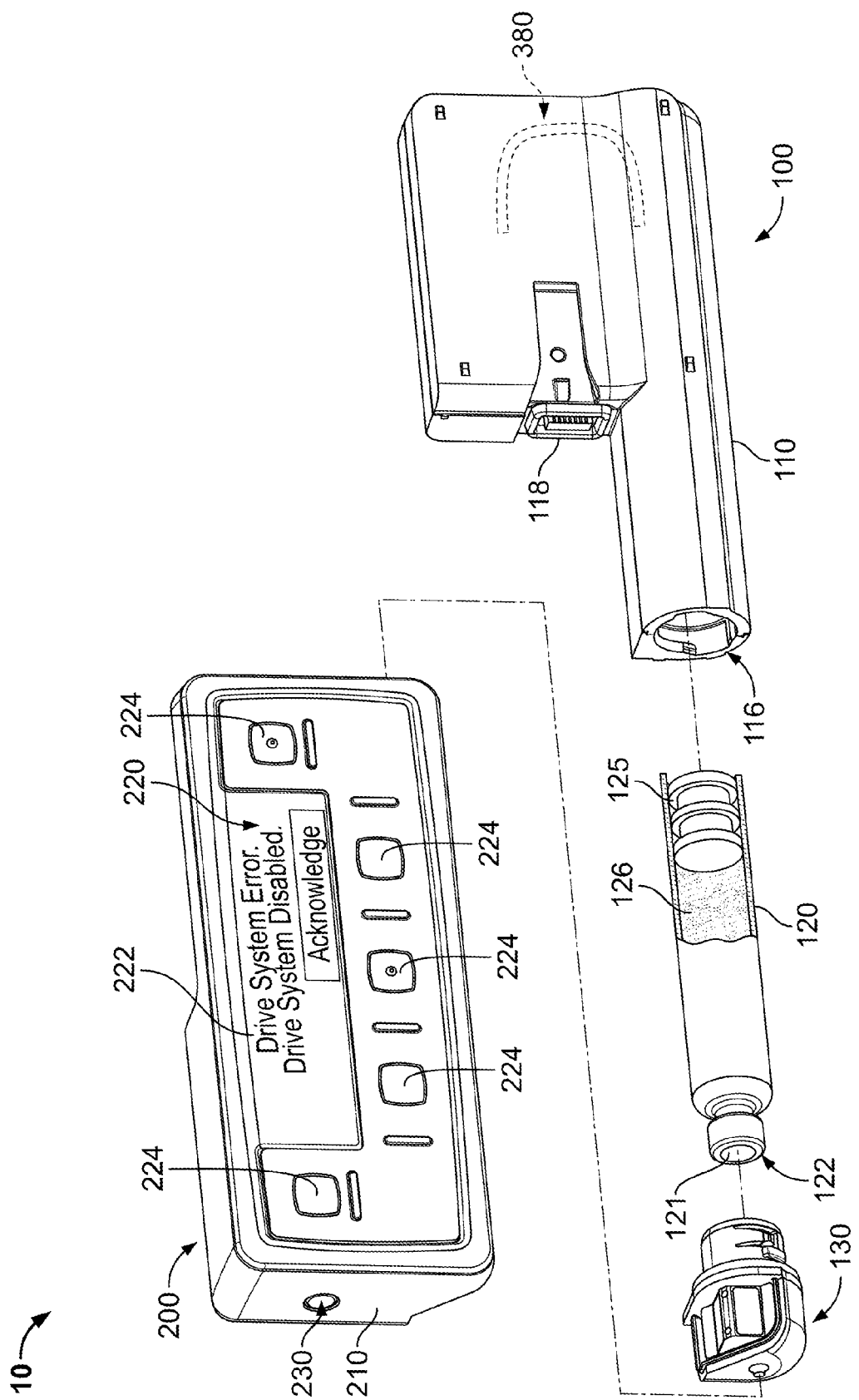
FIG. 1 is an exploded perspective view of an infusion pump system in accordance with some embodiments.

Referring to FIG. 1, an infusion pump system 10 can include a pump device 100 and a controller device 200 that communicates with the pump device 100. The pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system that advances a plunger 125 in the fluid cartridge 120 so as to dispense fluid therefrom.

Figure 7:
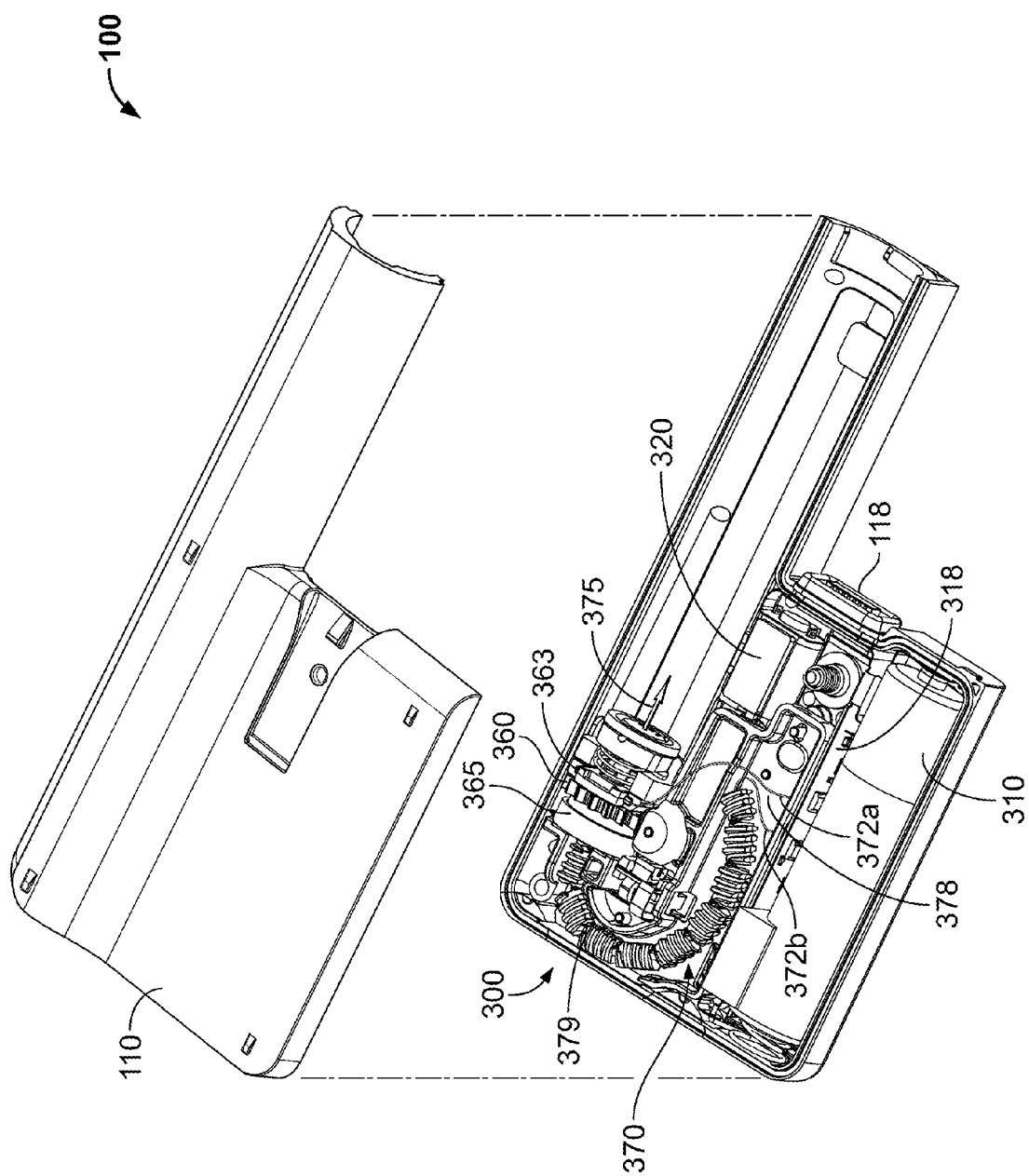
FIG. 7 is an exploded perspective view of the pump device of FIGS. 1-2 including a drive system detector, in accordance with some embodiments.

As described in more detail below in connection with FIGS. 7-11, some embodiments of the pump device 100 can include an internal drive system detector 380. In some embodiments, at least a portion of the drive system detector 380 comprises an electrically conductive element that is coupled to components of the drive system. For example, in the embodiment described in more detail below in connection with FIGS. 7-8, the drive system detector 380 includes an electrically conductive element coupled to a piston rod of the drive system and a software component stored in the control circuitry (of the controller device 200 in this embodiment) that is configured to periodically monitor the electrically conductive element. The drive system detector 380 can be configured to sense a change in impedance across the electrically conductive element when the pump device 100 has received an impact force that results in damage to the drive system 300 (FIG. 7). Examples of damage to the drive system may include where one or more components of the drive system 300 have sustained a partial fracture, complete breakage, or otherwise sustained damage that may affect the structural integrity of one or more components of the drive system 300. Where the drive system 300 sustains damage, the pump device 100 may potentially malfunction or otherwise cause over-dosage or under-dosage of medicine to the user. For example, in some situations, a user of the pump device 100 may expose the pump device 100 to an impact force. Depending on the magnitude of the impact force, the drive system 300 of the pump device 100 may be rendered inoperable for safe and accurate dispensation of medicine, and as such, some or all of the remaining medicine (e.g., in medicine cartridge 120) contained within pump device 100 may not be properly dispensed. In other words, an impact that may cause damage to the drive system 300 of the pump device 100 that can be detected using a drive system detector 380 that monitors at least one electrically conductive element coupled to one or more components of the drive system 300. Such an impact may occur, for example, by dropping the pump device 100 onto a floor or other hard surface.

When the pump device 100 and the controller device 200 are coupled (refer, for example, to FIG. 2), the drive system detector 380 can be in electrical communication with a circuit housed in the controller device 200. In such a case, if the drive system detector 380 previously detected damage to one or more components of the drive system 300, the infusion pump system 10 can be configured to initiate appropriate user safety countermeasures. If no such damage to the drive system was detected, the pump system 10 can proceed with normal operations. During normal operations, if the drive system detector 380 then detects damage to one or more components of the drive system 300, the pump system 10 can respond by initiating appropriate user safety countermeasures.

In some embodiments, the controller device 200 communicates with the pump device 100 to control the operation of the drive system. When the controller device 200, the pump device 100 (including the cap device 130), and the fluid cartridge 120 are assembled together, the user can (in some embodiments) conveniently wear the infusion pump system 10 on the user's skin under clothing, in a pouch clipped at the waist (e.g., similar to a cell phone pouch), or in the user's pocket while receiving the fluid dispensed from the pump device 100. Optionally, the controller device 200 may be configured as a reusable component that provides electronics and a user interface to control the operation of the pump device 100. In such circumstances, the pump device 100 can be a disposable component that is disposed of after a single use. For example, as described in more detail below in connection with FIGS. 4-5, the pump device 100 can be a "one time use" component that is thrown away after the fluid cartridge 120 therein is exhausted. Thereafter, the user can removably attach a new pump device 100' (having a new medicine cartridge 120') to the reusable controller device 200 for the dispensation of fluid from a new fluid cartridge 120'. Accordingly, the user is permitted to reuse the controller device 200 (which may include complex or valuable electronics, as well as a rechargeable battery) while disposing of the relatively low-cost pump device 100 after each use. Such a pump system 10 can provide enhanced user safety as a new pump device 100' (and drive system therein) is employed with each new fluid cartridge 120'.

Briefly, in use, the pump device 100 is configured to removably attach to the controller device 200 in a manner that provides a secure fitting, an overall compact size, and a reliable electrical connection that is resistant to water migration. For example, as described in more detail below in connection with FIGS. 1-5, the controller device 200 can include a housing 210 having a number of features that mate with complementary features of the pump housing 110. In such circumstances, the controller device 200 can removably attach with the pump device 100 in a generally side-by-side configuration. The compact size permits the infusion pump system 10 to be discrete and portable (as described below in connection with FIG. 3). Moreover, at least one of the pump device 100 or the controller device 200 can include a release member that facilitates an easy-to-use detachment and replacement process.

Referring again to FIG. 1, the pump system 10 can be a medical infusion pump system that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a medicine cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the medicine cartridge 120 after the medicine cartridge 120 is inserted into the cavity 116. For example, the pump housing structure 110 can include one or more retainer wings (not shown in FIG. 1) that at least partially extend into the cavity 116 to engage a portion of the medicine cartridge 120 when the medicine cartridge 120 is installed therein. Such a configuration may facilitate the "one-time-use" feature of the pump device 100. In some embodiments, the retainer wings can interfere with attempts to remove the medicine cartridge 120 from the pump device 100, thus ensuring that the pump device 100 will be discarded along with the medicine cartridge 120 after the medicine cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the medicine cartridge 120 is emptied, expired, or otherwise exhausted).

Still referring to FIG. 1, the controller device 200 can be removably attached to the pump device 100 so that the two components are mechanically mounted to one another in a fixed relationship. Such a mechanical mounting can form an electrical connection between the removable controller device 200 and the pump device 100. For example, the controller device 200 can be in electrical communication with a portion of a drive system (not shown in FIG. 1) of the pump device 100. As described in more detail below, the pump device 100 can include a drive system that causes controlled dispensation of the medicine or other fluid from the cartridge 120. In some embodiments, the drive system incrementally advances a piston rod (not shown in FIG. 1) longitudinally into the cartridge 120 so that the fluid is forced out of an output end 122. A septum 121 (FIG. 1) at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the medicine cartridge 120. Power signals, such as signals from the rechargeable battery 245 (refer to FIG. 6) of the controller device 200 and from the power source 310 (refer to FIG. 7) of the pump device 100 may also be passed between the controller device 200 and the pump device 100.

As shown in FIG. 1, the pump device 100 can include an electrical connector 118 (e.g., having conductive pads, pins, and the like) that is exposed to the controller device 200 and that mates with a complementary electrical connector (refer to connector 218 in FIG. 2) on the adjacent face of the controller device 200. The electrical connectors 118 and 218 provide the electrical communication between the control circuitry (refer, for example, to FIG. 6) housed in the controller device 200 and at least a portion of the drive system or other components of the pump device 100. For example, in some embodiments, the electrical connectors 118 and 218 can permit the transmission of electrical control signals to the pump device 100 and the reception of feedback signals (e.g., sensor signals) from particular components within the pump device 100. The electrical connectors 118 and 218 may similarly facilitate transmission of one or more power signals from the rechargeable battery pack 245 to the pump device 100, where the signals may be used to provide power to components of the pump device 100, or to transmit one or more power signals from the power source 310 to the controller device, where the signals may be used to charge the rechargeable battery 245 or to power components of the controller device 200.

Still referring to FIG. 1, the controller device 200 can include a user interface 220 that permits a user to monitor the operation of the pump device 100. In some embodiments, the user interface 220 can include a display device 222 and one or more user-selectable buttons (e.g., several buttons 224 are shown in the embodiment of FIG. 1). The display device 222 can include an active area in which numerals, text, symbols, images, or a combination thereof can be displayed. For example, the display device 222 can be used to communicate a number of settings or menu options for the infusion pump system 10. In this embodiment, the user may press one or more of the buttons to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). In some embodiments, the user can adjust the settings or otherwise program the controller device 200 by pressing one or more buttons of the user interface 220. For example, in embodiments of the infusion pump system 10 configured to dispense insulin, the user may press one or more of the buttons to change the dispensation rate of insulin or to request that a bolus of insulin be dispensed immediately or at a scheduled, later time. In some implementations, the display device 222 may also be used to communicate information regarding remaining battery life.

Accordingly, when the controller device 200 is connected to the pump device 100, the user can be provided with the opportunity to readily monitor the infusion pump operation by simply viewing the user interface 220 of the controller device 200 connected to the pump device 100. Such monitoring capabilities may provide comfort to a user who may have urgent questions about the current operation of the pump device 100. Also, in these embodiments, there may be no need for the user to carry and operate a separate module to monitor the operation of the pump device 100, thereby simplifying the monitoring process and reducing the number of devices that must be carried by the user. If a need arises in which the user desires to monitor the operation of the pump device 100 or to adjust the settings of the pump system 10 (e.g., to request a bolus amount of medicine), the user can readily operate the user interface 220 of the controller device 200, which is removably attached to the pump device 100, without the requirement of locating and operating a separate monitoring module.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas.

The inspection light device 230 can also be used to notify the user to an alert condition of the pump system 10. For example, as described further in reference to FIG. 12 below, the inspection light device 230 can be activated when the drive system detector 380 has detected damage to one or more components of the drive system 300. An activation of the inspection light device 230 can thereby provide a visual notification (as an alternative to, or in addition to, the visual notification provided on the display device 222) to the user that attention to the pump system 10 is warranted.

Figure 2:
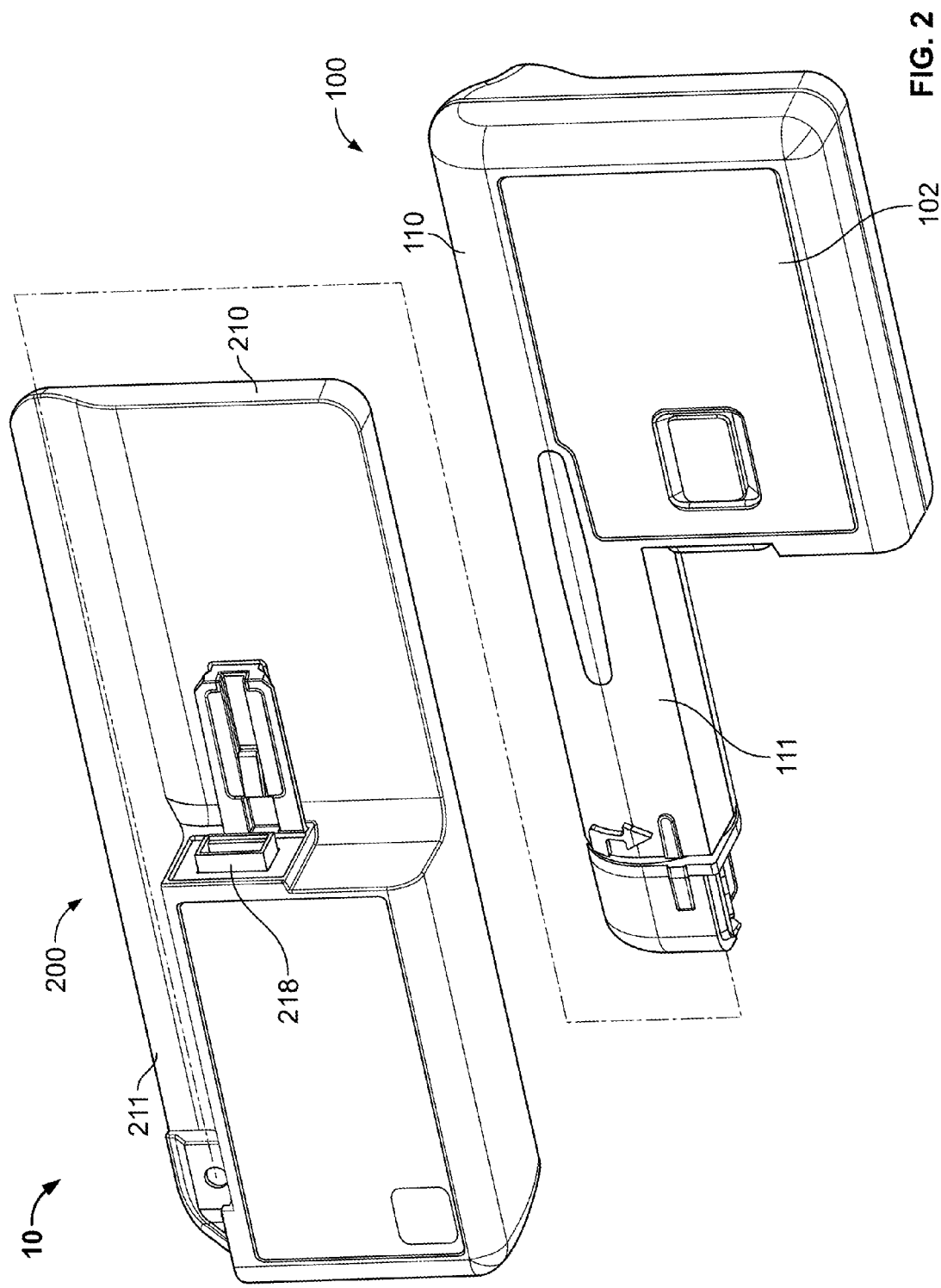
FIG. 2 is a perspective view of the infusion pump system of FIG. 1 in a detached state.

Referring now to FIG. 2, when the infusion pump system 10 operates, the controller device 200 can be removably attached to the pump device 100 in a side-by-side arrangement. For example, the pump device 100 may be moved in a longitudinal direction (e.g., refer to direction 219 in FIG. 4) toward the controller device 200 until the complementary features connect and secure the separate components in the side-by-side arrangement. The controller device 200 can include a controller housing structure 210 having a number of features that are configured to mate with complementary features of the pump housing structure 110 so as to form a releasable mechanical connection. For example, the pump housing structure 110 can include a barrel 111 that mates with a complementary barrel channel 211 of the controller housing 210. In various implementations, the pump device 100 and the controller device 200 can be mounted to one another so that the assembled system 10 is resistant to water migration both into the pump housing structure 110 and the controller housing structure 210. Such a configuration can also provide water-resistant protection for the electrical connection between the pump device 100 and the controller device 200. Thus, the sensitive internal components in the controller device 200 and the pump device 100 can be reliably protected from water migration if the user encounters water (e.g., rain, incidental splashing, and the like) while using the pump system 10.

Figure 3:
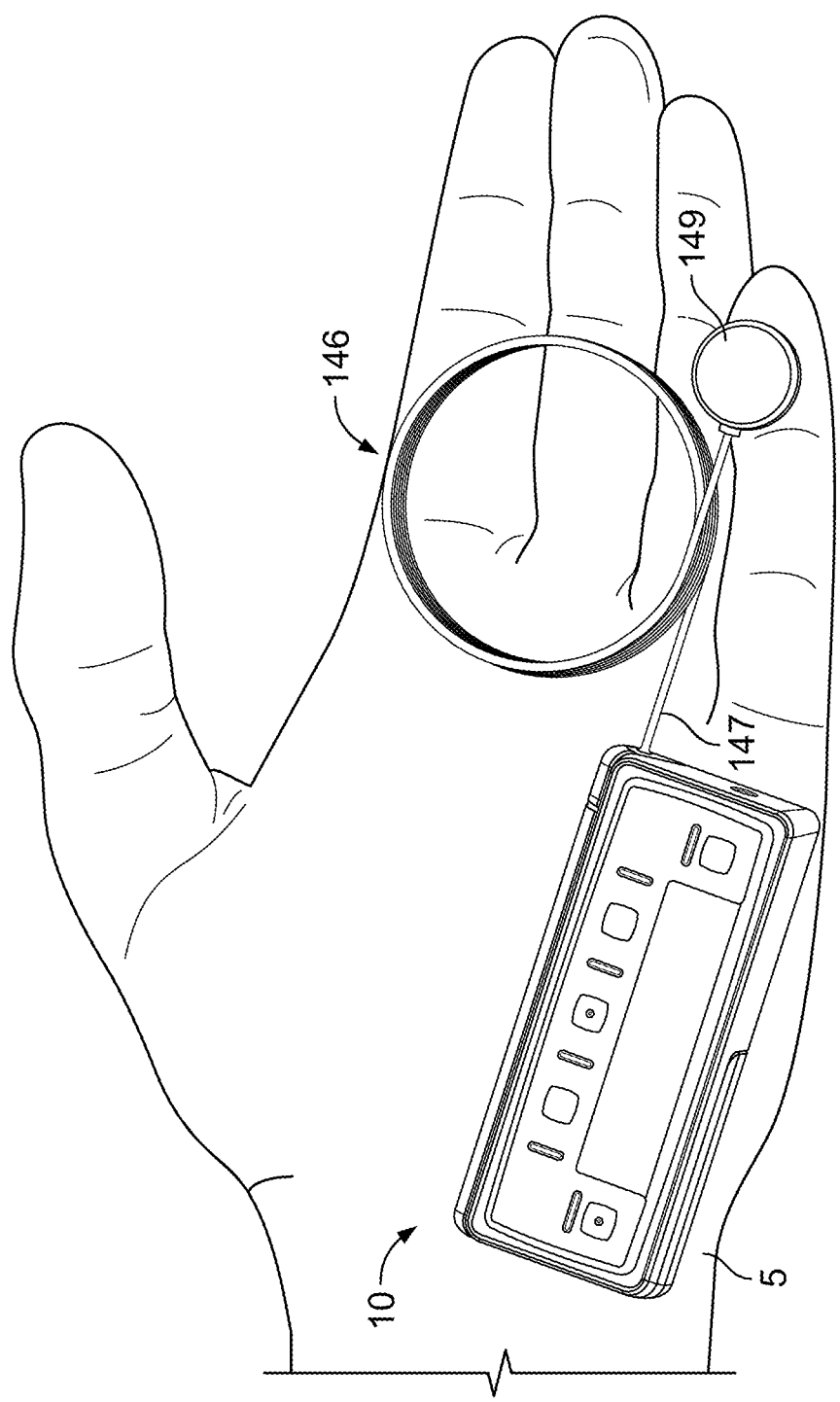
FIG. 3 is a perspective view of an infusion pump system, in accordance with some embodiments.

Referring to FIG. 3, the infusion pump system 10 can be configured to be portable and can be wearable and concealable. For example, a user can conveniently wear the infusion pump system 10 on the user's skin (e.g., skin adhesive) underneath the user's clothing or carry the pump device 100 in the user's pocket (or other portable location) while receiving the medicine dispensed from the pump device 100. The pump system 10 is shown in FIG. 3 as being held in a user's hand 5 so as to illustrate an exemplary size of the system 10 in accordance with some embodiments. This embodiment of the infusion pump system 10 is compact so that the user can wear the portable infusion pump system 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. In general, the infusion set 146 can be a tubing system that connects the infusion pump system 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 1) of the medicine cartridge 120 and the tube 147 of the infusion set 146.

In some embodiments, the infusion pump system 10 can be pocket-sized so that the pump device 100 and controller device 200 can be worn in the user's pocket or in another portion of the user's clothing. In some circumstances, the user may desire to wear the pump system 10 in a more discrete manner. Accordingly, the user can pass the tube 147 from the pocket, under the user's clothing, and to the infusion site where the adhesive patch can be positioned. As such, the pump system 10 can be used to deliver medicine to the tissues or vasculature of the user in a portable, concealable, and discrete manner.

In some embodiments, the infusion pump system 10 can be configured to adhere to the user's skin directly at the location in which the skin is penetrated for medicine infusion. For example, a rear surface 102 (FIG. 2) of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Referring now to FIGS. 4-5, the infusion pump system 10 can be operated such that the pump device 100 is a disposable, non-reusable component while the controller device 200 is a reusable component. In these circumstances, the pump device 100 may be configured as a "one-time-use" device that is discarded after the medicine cartridge is emptied, expired, or otherwise exhausted. Thus, in some embodiments, the pump device 100 can be designed to have an expected operational life of about 1 day to about 30 days, about 1 day to about 20 days, about 1 to about 14 days, or about 1 day to about 7 days-depending on the volume of medicine in the cartridge 120, the dispensation patterns that are selected for the individual user, and other factors. For example, a medicine cartridge 120 containing insulin can have an expected usage life of about 7 days after the cartridge is removed from a refrigerated state and the septum 121 is punctured. In some circumstances, the dispensation pattern selected by the user can cause the insulin to be emptied from the medicine cartridge 120 before the 7-day period. If the insulin is not emptied from the medicine cartridge 120 after the 7-day period, the remaining insulin can become expired sometime thereafter. In either case, the pump device 100 and the medicine cartridge 120 therein can be collectively discarded after exhaustion of the medicine cartridge 120 (e.g., after being emptied, expired, or otherwise not available for use).

The controller device 200, however, may be reused with subsequent new pump devices 100' and new medicine cartridges 120'. As such, the control circuitry, the user interface components, the rechargeable battery pack 245, and other components that may have relatively higher manufacturing costs can be reused over a longer period of time. For example, in some embodiments, the controller device 200 can be designed to have an expected operational life of about 1 year to about 7 years, about 2 years to about 6 years, or about 3 years to about 5 years—depending on a number of factors including the usage conditions for the individual user. Accordingly, the user can be permitted to reuse the controller device 200 (which can include complex or valuable electronics, and a rechargeable battery pack) while disposing of the relatively low-cost pump device 100 after each use. Such a pump system 10 can provide enhanced user safety as a new pump device 100' (and drive system therein) is employed with each new medicine cartridge 120'.

Referring to FIGS. 4-5, the same controller device 200 can be reused with a new pump device 100' having a new medicine cartridge 120' retained therein, and the previously used pump device 100, including the exhausted medicine cartridge, can be discarded in a discard bin 20. The new pump device 100' (FIG. 4) can have a similar appearance, form factor, and operation as the previously used pump device 100, and thus the new pump device 100' can be readily attached to the controller device 200 for controlled dispensation of medicine from the new medicine cartridge 120'. In some embodiments, the user can prepare the new pump device 100' for use with the controller device 200. For example, the user may insert the new medicine cartridge 120' in the cavity 116 of the new pump device 100' and then join the cap device 130 to the pump housing to retain the new medicine cartridge 120' therein (refer, for example, to FIG. 1). Although the tubing 147 of the infusion set 146 is not shown in FIG. 4, it should be understood that the tubing 147 can be attached to the cap device 130 prior to the cap device 130 being joined with the housing 110. For example, a new infusion set 146 can be connected to the cap device 130 so that the tubing 147 can be primed (e.g., a selected function of the pump device 100 controlled by the controller device 200) before attaching the cannula's adhesive patch to the user's skin. As shown in FIG. 4, the new medicine cartridge 120' may be filled with medicine such that the plunger 125 is not viewable through the barrel 111.

The new pump device 100' can be removably attached to the controller device 200 to assemble into the infusion pump system 10 for delivery of medicine to the user. As previously described, the guided motion in the longitudinal direction 219 provides the user with a convenient "one-movement" process to attach the pump device 100' and the controller device 200. For example, the user can readily slide the pump device 100' and the controller device 200 toward one another in a single movement (e.g., in the longitudinal direction 219) that causes both a physical connection and an electrical connection. Thus, the infusion pump system 10 can permit users to readily join the pump device 100' and the controller device 200 without compound or otherwise difficult hand movements—a feature that can be particularly beneficial to child users or to elderly users.

Figure 6:
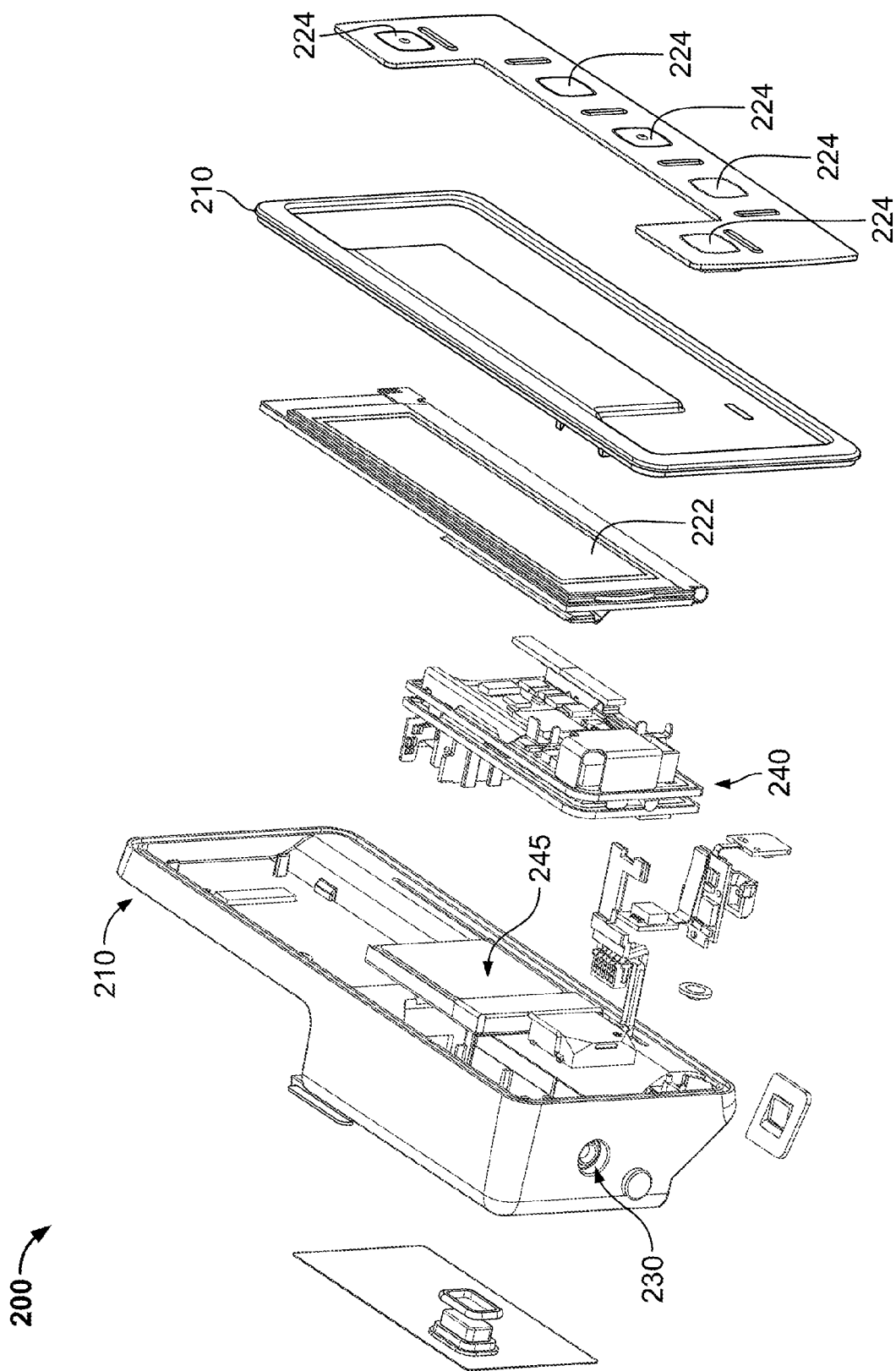
FIG. 6 is an exploded perspective view of a controller device for an infusion pump system, in accordance with some embodiments.

Referring now to FIG. 6, the controller device 200 (shown in an exploded view) houses a number of components that can be reused with a series of successive pump devices 100. In particular, the controller device 200 can include controller circuitry 240 and a rechargeable battery pack 245, each arranged in the controller housing 210. As described above, rechargeable battery pack 245 may provide electrical energy to components of controller circuitry 240, other components of the controller device (e.g., a display device 222 and other user interface components, sensors, or the like), or to components of the pump device 100. Controller circuitry 240 may be configured to communicate control or power signals to the drive system of the pump device 100, or to receive power or feedback signals from the pump device 100.

Still referring to FIG. 6, the user interface 220 of the controller device 200 can include input components and/or output components that are electrically connected to the controller circuitry 240. For example, the user interface 220 can include the display device 222 having an active area that outputs information to a user and buttons 224 that the user can use to provide input. Here, the display device 222 can be used to communicate a number of settings or menu options for the infusion pump system 10. In some embodiments, the controller circuitry 240 can receive input commands from a user's button selections and thereby cause the display device 222 to output a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining the cartridge 120, the amount of battery life remaining, or the like). The controller circuitry 240 can be programmable to cause the controller circuitry 240 to change any one of a number of settings for the infusion pump system 10. For example, the user may provide one or more instructions to adjust a number of settings for the operation of the infusion pump system 10. Such settings may be stored in one or more memory devices arranged in the controller circuitry 240.

As shown in FIG. 6, the infusion pump system 10 can be equipped with the inspection light device 230 to conveniently aid in visual inspection processes. For example, visual inspection and possible change of the infusion set 146 may be required in less than optimal conditions, including low-light conditions. Likewise, visual inspection of the pump housing cavity 116 (and the medicine cartridge 120 therein) may be required in low-light conditions. The user interface 220 of the controller device 200 can include an illuminated display screen 222 to facilitate the user's view of the display screen 222, but the inspection light device 230 provides a dedicated light source for illuminating targeted sites external to the controller device 200, for providing an alert notification, or a combination thereof.

The inspection light device 230 can include one or more user triggered light sources that are positioned to direct illumination at targeted objects outside of the pump system 10 or at components of the pump device 100. In the embodiment depicted in FIG. 6, the light source is arranged on the controller device 200. Such an arrangement provides close proximity to the control circuitry 240 housed in the controller device 200, thereby permitting the light source of the inspection light device 230 to be electrically connected to the control circuitry. In other embodiments, could be arranged on the pump device 100 or on both the controller device 200 and the pump device 100.

The inspection light device 230 can also be used to provide a visual notification to the user in the event of an alert or alarm condition. For example, as described further in reference to FIG. 12, the inspection light device 230 can be activated in response to detection by the drive system detector 380 of damage to one or more components of the drive system 300 (e.g., where pump system 10 sustains an impact force), which may cause a malfunction of the pump system 10.

In some optional embodiments, the controller circuitry 240 can include a cable connector (e.g., a USB connection port or another data cable port) that is accessible on an external portion of the controller housing 210. As such, a cable can be connected to the controller circuitry 240 to upload data or program settings to the controller circuitry or to download data from the controller circuitry. For example, historical data of medicine delivery can be downloaded from the controller circuitry 240 (via the cable connector) to a computer system of a physician or a user for purposes of analysis and program adjustments. Optionally, the data cable can also provide recharging power.

Referring now to FIG. 7, the pump device 100 can include a drive system 300 that is controlled by the controller device 200. As described in more detail below, the drive system 300 can incrementally dispense fluid in a controlled manner from cartridge 120 inserted into the pump device 100. In addition, as described in more detail below, one or more components of the drive system 300 may comprise an electrically conductive element or material so that an electrical current can be passed through the one or more components of the drive system. In this example, the flexible piston rod 370 can include electrically conductive strips mounted thereto, can include electrically conductive wires embedded or attached thereto, or can be manufactured using an electrically conductive polymer. Moreover, the flexible piston rod 370 can be electrically connected to a printed circuit board 318 housed in the pump device 100. As such, the voltage across the flexible piston rod 370 may be monitored, for example, by a software component (not shown) of the drive system detector 380. For example, the software component of the drive system detector 380 can be stored in computer-readable memory housed in the controller device 200 (e.g., as part of the control circuitry) or on the printed circuit board 318 (and in communication with the control circuitry of the controller device 200). The software component of the drive system detector 380 can periodically query the voltage level across the flexible piston rod 370. For example, the one or more electrically conductive strips mounted to the flexible piston rod 370 may be electrically connected to the controller device 200 (e.g., using wires 372a and 372b and the printed circuit board 318 that is connected via the connectors 118, 218) so that an electrical ground and voltage readings can be monitored by the software component of the drive system detector 380 stored in the control circuitry in the controller device 200. In this example, when the software component of the drive system detector 380 queries the voltage across the piston 370 and where the detected voltage is substantially zero (e.g., ground), the drive system 300 is likely operating as intended without damage to the piston rod 370. However, where the detected voltage across the piston rod 370 is substantially greater than zero (e.g., a high signal, not ground), the drive system 300 may be broken or otherwise damaged (e.g., because the one or more electrically conductive strips mounted to the flexible piston rod 370 are likely broken, indicating that the piston rod 370 is broken). In such circumstances, the pump system 10 can respond to the detection of the damaged piston rod 370 by initiating appropriate user safety countermeasures.

In the illustrated embodiment shown in FIG. 7, at least a single strip of conductive material 379 is shown affixed to the flexible piston rod 370. This flexible material can be any conductive material that can be attached to another surface. Examples include, but are not limited to, conductive wires, conductive paint, or other conductive materials such as conductive polymers. To provide an accurate measurement of the voltage measurement of the flexible piston rod 370, a first wire 372a or other electrically conductive material is connected to the lead end of the conductive strip 379 on the flexible piston rod 370, and a second wire 372b or other electrically conductive material is attached to the trailing end of the conductive strip 379. One or both of the wires 372a-b can be directly attached to the respective end of the conductive strip 379 (e.g., directly soldered thereto, or the like). Alternatively, one of both of the wires 372a-b can be connected to the respective end of the conductive strip using a wiper connection in which an electrical connection is formed across a sliding engagement between a wiper element and the conductive strip 379. It should be understood from the description herein that alternative embodiments are not limited to the configuration in which the first wire 372a connects to the conductive strip 379 at an opposite end from the second wire 372b. Rather, is some alternative embodiments, both wires can be connected to respective conductive strips at the trailing end of the piston rod 370 or at the leading end of the piston rod 370 (refer, for example, to first and second wires 372a-b as depicted FIGS. 8-11).

Still referring to FIG. 7, the printed circuit board 318 of the pump device 100 may serve as a connector circuit to facilitate the transfer of signals to and from the electrical connector 118. In some implementations, the connector circuit in the pump device 100 may include a memory device that can store data regarding the pump device 100 and its operational history. As previously described, the electrical connector 118 of the pump device 100 can mate with the connector 218 (FIG. 2) of the controller device 200 so that electrical communication can occur between the pump device 100 and the controller device 200. The connector circuit can also operate as a passageway for the electrical power from a power source 310 housed in the pump device 300 to pass to the controller device 200 for recharging of the rechargeable battery 245. Furthermore, the connector circuit can operate as a passageway for feedback signals from the drive system 300 to the controller circuitry 240 of the controller device 200. For example, the controller device 200 can monitor the voltage value across the electrically conductive element of the piston rod 370 using the connector circuit, which receives the wires 372a and 372b or other electrical connections extending from the electrically conductive element of the piston rod 370. Such signals can be used by the controller device to determine the operational status of the drive system 300.

In this embodiment, the pump device 100 houses the drive system 300 and the power source 310. For example, the power source 310 may comprise an alkaline battery cell, such as a 1.5 Volt "AAA" alkaline battery cell, which is contained in a dedicated space of the pump housing structure 110. The power source 310 may be capable of transmitting electrical energy to the controller device 200 when the pump device 100 is attached to the controller device 200, via connectors 118 and 218 as described above. For example, the power source 310 may be used to charge the rechargeable battery pack 245 when the pump device 100 is attached to the controller device 200. In some embodiments, the power source 310 is used to provide energy to the drive system 300 of the pump device 100, and also to electronic components of the controller device 200. In particular embodiments, the power source 310 may provide the energy to power all aspects of the infusion pump system 10. In some alternative embodiments, the rechargeable battery 245 housed in the controller 200 may provide the energy to power all aspects of the infusion pump system 10. In other embodiments, the rechargeable battery 245 and the power source 310 may each be responsible for powering particular aspects of the infusion pump system 10. In further embodiments, the rechargeable battery 245 may provide the energy to supplement the energy provided by the power source 310 to power aspects of the infusion pump system.

Still referring to FIG. 7, in some embodiment, the drive system 300 may include a number of components, such as an electrically powered actuator (e.g., reversible motor 320 or the like), a drive wheel 360, a bearing 365, a flexible piston rod 370, a piston rod guide 363, and a plunger engagement device 375. In this embodiment, the reversible motor 320 drives a gear system (not shown in FIG. 7) to cause the rotation of the drive wheel 360 that is coupled with the bearing 365. The drive wheel 360 may include a central aperture with an internal thread pattern, which mates with an external thread pattern on the flexible piston rod 370. The interface of the threaded portions of the drive wheel 360 and flexible piston rod 370 may be used to transmit force from the drive wheel to the piston rod 370. Accordingly, in the embodiment of FIG. 7, the drive wheel 360 is the driver while the flexible piston rod 370 is the driven member. As further described below, the rotation of the drive wheel 360 can drive the flexible piston rod 370 forward in a linear longitudinal direction.

Referring now to FIGS. 8-11, various example embodiments of the flexible piston rod 370 are shown. As described above, the flexible piston rod 370 can include an electrically conductive element, such as electrically conductive strips mounted thereto, electrically conductive wires embedded or attached thereto, or electrically conductive polymer that forms the piston rod 370. The electrically conductive element of the piston rod 370 can be connected to the electrical connection circuit 318, for example, using flexible wires 372a and 372b. Furthermore, in a preferred embodiment, one of the wires 372a and 372b is connected to an electrical ground. As such, when an electrical current is passed through the electrically conductive flexible piston rod 370, a voltage reading of the flexible piston rod 370 is substantially zero so long as the flexible piston rod's 370 structural integrity has not been compromised (e.g., because of damage sustained when the pump device 100 is dropped). Also, in these embodiments described in connection with FIGS. 8-11, both wires 372a and 372b can be attached to the trailing end of the flexible piston rod 370, thereby reducing the likelihood that the wires 372a and 372b would being entangled with a portion of the medicine cartridge 120 or the drive system (e.g., any part of a combination of the drive wheel 360, piston rod guide 363, and bearing 365) as the leading end of the flexible piston rod 370 moves forward in a linear longitudinal direction.

Figure 8:
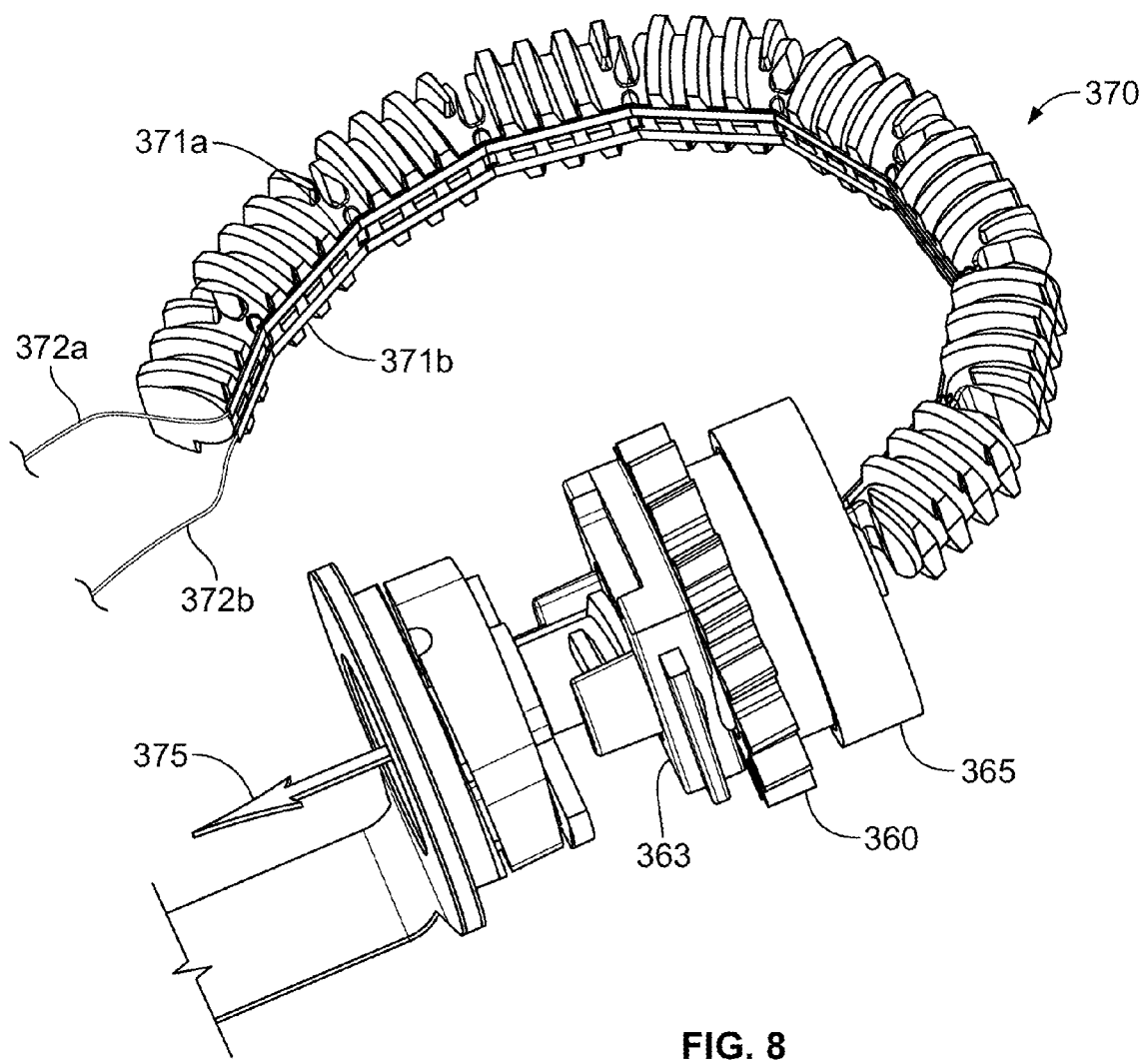
FIG. 8 is a perspective view of a portion of an alternative drive system detector for use in the pump device of FIG. 7, in accordance with some embodiments.

As shown in FIG. 8, the electrically conductive element of the drive system detector 380 may comprise one or more conductive strips 371 extending generally continuous along outer surface of the flexible piston rod 370. For example, in one embodiment, silver conductive paint strips 371a and 371b can be applied to the surface of the flexible piston rod 370 (across the segments and the hinge portions between adjacent segments). Such conductive paint allows electrical current to be applied across the flexible piston rod 370 and periodic voltage readings queried by the software component of the drive system detector 380. In situations where, for example, the flexible piston rod 370 is fractured or is otherwise partially or completely severed, one or more segments of at least one of the conductive strips 371a and 371b will also likely be severed. As such, because the electrical connection is disrupted, the flexible piston rod 370 is no longer electrically connected to ground. Therefore, when the drive system detector 380 takes a voltage reading, the voltage reading will likely be a substantially non-zero value indicating a malfunction of the drive system 300.

Figure 9:
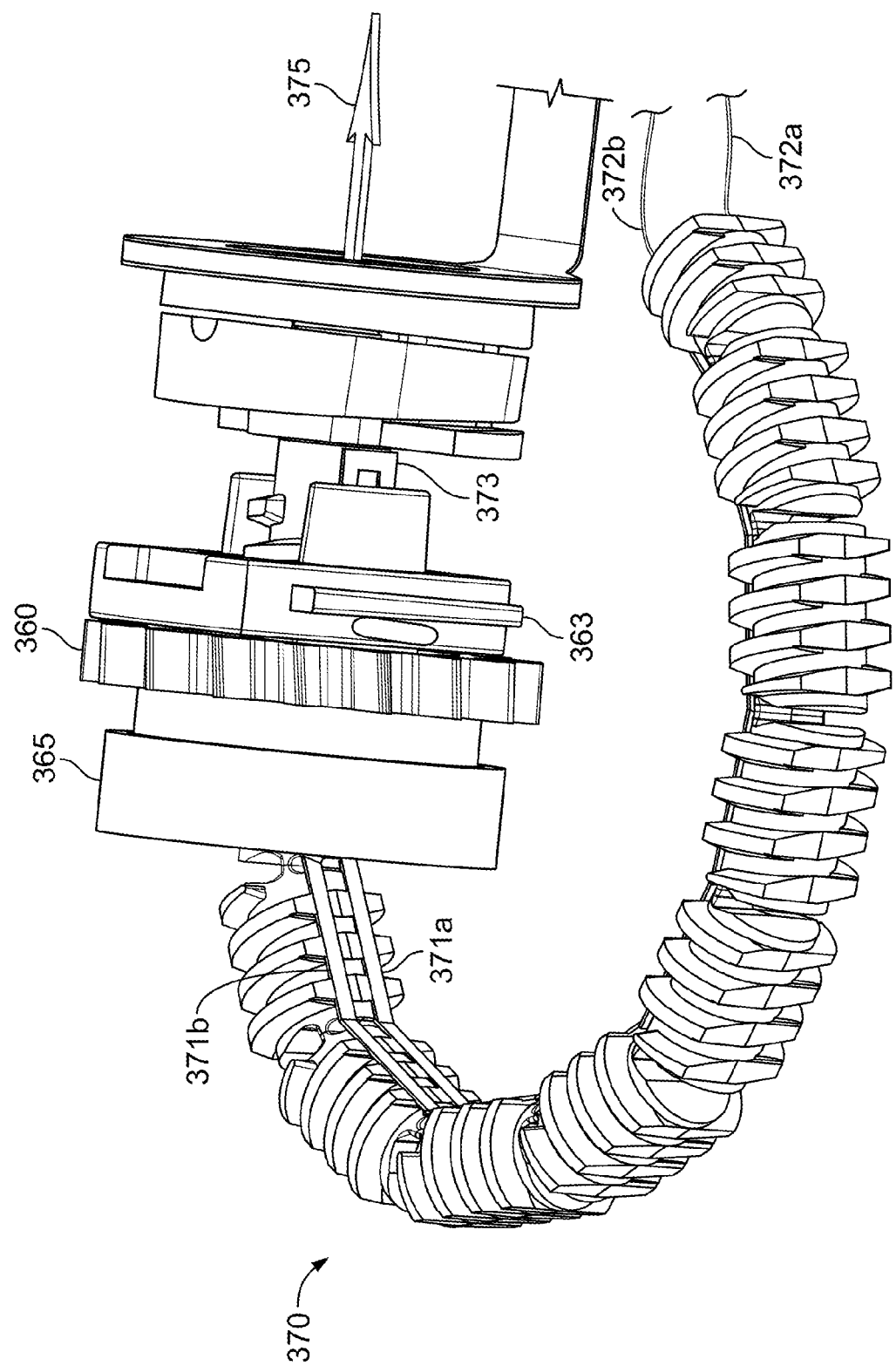
FIG. 9 is another perspective view of the portion of the alternative drive system detector of FIG. 8.

Referring now to FIG. 9, a loop back 373 of the conductive strips 371a and 371b is shown. In essence, the use of the loop back 373 creates a single U-shaped conductive path that includes conductive strips 371a and 371b and loop back 373. One advantage of such an arrangement is that the flexible wires 372a and 372b are connected at the same end of the piston rod 370 (e.g., the trailing end portion in this embodiment). As such, there is no need for a wire connection at the leading end of the piston rod 370 that advances into the medicine cartridge 120 (FIG. 1) as the medicine is dispensed. Again, when any portion of the conductive strips 371a and 371b or loop back 373 are severed or otherwise sustain damage, the electrical connection to the electrical ground is disrupted and subsequent voltage readings will likely be substantially non-zero values indicating a malfunction of the drive system 300.

Figure 10:
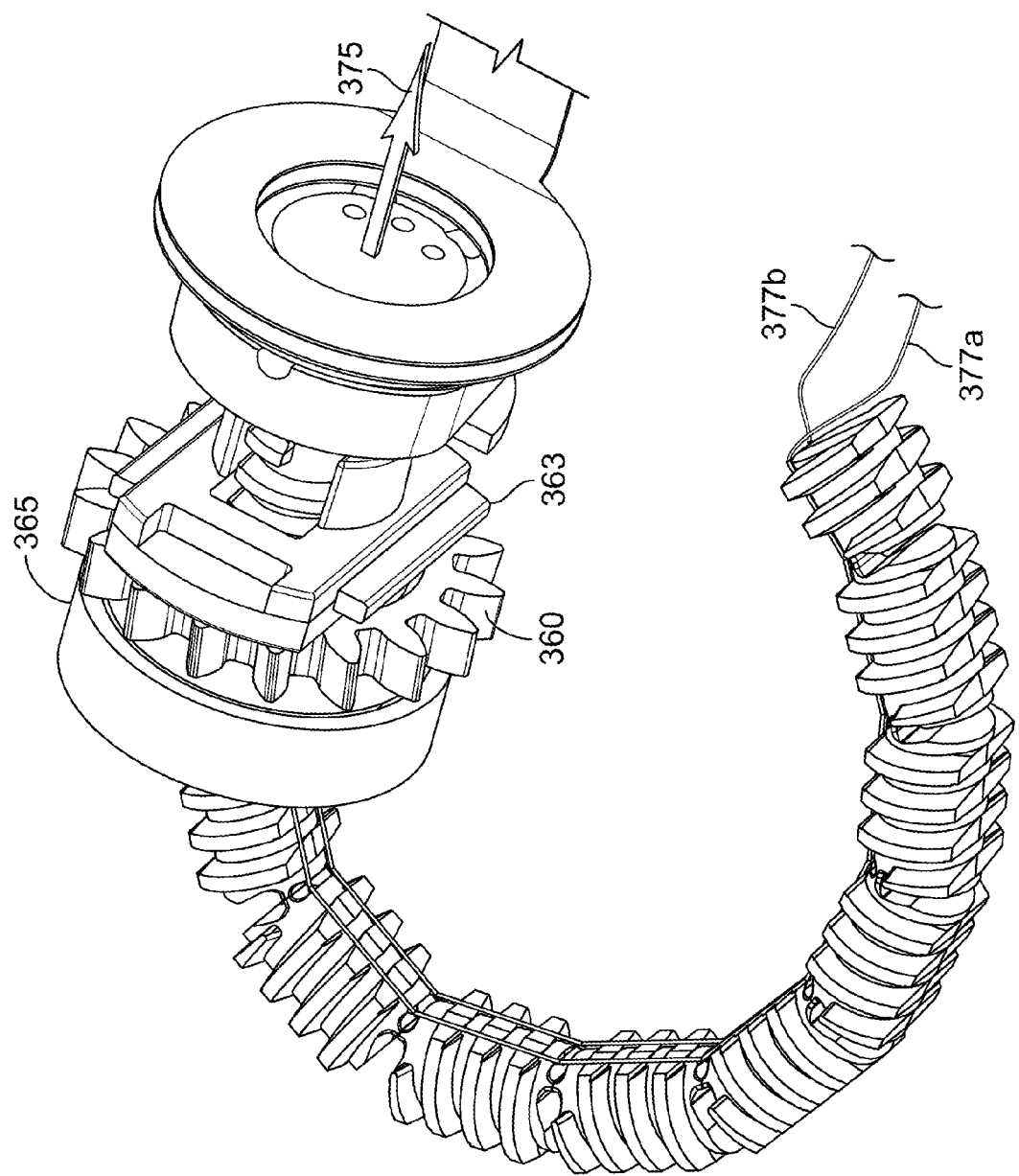
FIG. 10 is a perspective view of a portion of an alternative drive system detector for use in the pump device of FIG. 7, in accordance with some embodiments.

Referring now to FIG. 10, in this embodiment, the electrically conductive element of the drive system detector 380 comprises one or more conductive wires 377 applied to a generally continuous outer surface of the flexible piston rod 370. For example, in one embodiment, flexible conductive wires 377a and 377b can be applied to the surface of the flexible piston rod 370 (across the segments and the hinge portions between adjacent segments). In some embodiments, the wires 377a and 377b are sheathed in an insulating material, such as a non-conductive flexible polymer or other covering. Such flexible wires allow electrical current to be applied across the flexible piston rod 370 and periodic voltage readings queried by the software component of the drive system detector 380 (as previously described). In addition, in some embodiments, the flexible wires 377a and 377b may be different portions of a single wire that are joined at a loopback near the leading end of the piston rod (similar to the loopback 373 shown in FIG. 9), thereby creating a single U-shape conductive path. Again, as previously described in connection with FIG. 9, one advantage of such an arrangement is that the flexible wire portions 377a and 377b extend from the same end of the piston rod 370 (e.g., the trailing end portion in this embodiment) toward the printed circuit board 318. In such circumstances, there is no need for a wire connection at the leading end of the piston rod 370 that advances into the medicine cartridge 120 (FIG. 1) as the medicine is dispensed. In situations where, for example, the flexible piston rod 370 is fractured or is otherwise partially or completely severed, one or more segments of at least one of the flexible wires 377a and 377b may also be severed. In such circumstances, because the electrical path across the piston rod 370 is disrupted, the flexible piston rod 370 is no longer electrically connected to ground. Therefore, when the software component of the drive system detector 380 queries a voltage reading, the voltage reading will likely be a substantially non-zero value (e.g., a high signal, not ground) indicating the drive system 300 may be broken or otherwise damaged.

Referring now to FIGS. 11A-B, some alternative embodiments of the drive system detector 380 may employ one or more conductive wires 377 embedded within the piston rod 370. One example of the embedded wires 377 are depicted in an unmagnified view (as shown in FIG. 11A) and a magnified view (as shown in FIG. 11B). In this embodiment, the one or more conductive wires 377 are disposed within corresponding interior channels or cavities of the flexible piston rod 370. For example, in one embodiment, flexible conductive wires 377a and 377b can be threaded through one or more mostly internal channels (and across the segments and the hinge portions between adjacent segments) created when the flexible piston rod 370 is at least partially manufactured using an insert molding technique. For example, FIG. 11B illustrates a magnified view of a number of hinge portions of the flexible rod 370 whereby only a portion of the wires 377a and 377b internal to the flexible piston rod 370 are visible.

In some embodiments, the wires 377a and 377b are sheathed in an insulating material, such as a non-conductive flexible polymer or other covering. Such flexible wires allow electrical current to be applied across the flexible piston rod 370 and periodic voltage readings queried by the software component of the drive system detector 380. In addition, in some embodiments, the flexible wires 377a and 377b may be different portions of a single wire that are joined at a loopback near the leading end of the piston rod (similar to the loopback 373 shown in FIG. 9), thereby creating a single U-shape conductive path. Again, as previously described in connection with FIG. 9, one advantage of such an arrangement is that the flexible wire portions 377a and 377b extend from the same end of the piston rod 370 (e.g., the trailing end portion in this embodiment) toward the printed circuit board 318. In such circumstances, there is no need for a wire connection at the leading end of the piston rod 370 that advances into the medicine cartridge 120 (FIG. 1) as the medicine is dispensed. In situations where, for example, the flexible piston rod 370 is fractured or is otherwise partially or completely severed, one or more segments of at least one of the flexible wires 377a and 377b may also be severed at least in part due to their respective integration into the internal structure of the flexible piston rod 370. In such circumstances, because the electrical path across the piston rod 370 is disrupted, the flexible piston rod 370 is no longer electrically connected to ground. Therefore, when the software component of the drive system detector 380 queries a voltage reading, the voltage reading will likely be a substantially non-zero value (e.g., a high signal, not ground) indicating the drive system 300 may be broken or otherwise damaged.

In addition to the present embodiments of FIGS. 8-11, other embodiments that provide for an electrically conductive and flexible piston rod 370 are also possible. For example, the piston rod 370 can be constructed using an electrically conductive polymer material. In such an embodiment, when the flexible piston rod 370 fractures or otherwise loses structural integrity, the electrical connection to ground is disrupted and a voltage reading of the piston rod 370 will likely be a substantially non-zero value. Again, such a higher voltage value (e.g., not ground) generally indicates damage sustained by the flexible piston rod 370 and a possible malfunction of the drive system 300. Where such a malfunction is detected, the infusion pump system 10 can initiate appropriate user safety countermeasures, described in more detail below.

Accordingly, the drive system detector 380 described in some or all of the aforementioned embodiments can include at least: (1) an electrically conductive element coupled to a piston rod 370 or other component of the drive system 300, and (2) a software component stored in the control circuitry 240 (FIG. 6) that is configured to periodically query or otherwise monitor the electrically conductive element. The drive system detector 380 can be configured to sense a change in impedance across the electrically conductive element after the pump device 100 has received an impact force that results in damage to the drive system 300.

In general, the drive system detector 380 can operate in three different modes: (1) a "normal" mode where pump device 100 and controller device 200 are coupled together, and the conductive element (e.g., the one or more conductive strips, wires or material extending along the piston rod 370 or other component of the drive system 300) is intact; (2) a "damage-detected" mode where the pump device 100 and the controller device 200 are coupled together, but said conductive element coupled to the drive system 300 is broken; and (3) a "disconnected" mode where the pump device 100 and the controller device 200 are not electrically connected, yet the drive system detector 380 passively detects that the pump device 100 has sustained possible damage to the drive system 300 therein.

For example, in the aforementioned "normal" mode—where pump device 100 and controller device 200 are coupled together, and the conductive element coupled to the drive system 300 is not broken—a voltage applied across the conductive element will indicate a first signal type (e.g., a ground or "low" signal that is detected by the software component of the drive system detector 380). As a result of the drive system detector 380 detecting the ground signal or "low" signal, the control circuitry 240 will operate the pump system 10 is in the "normal" mode (e.g., dispensation of the medicine can proceed, along with other pump operations). The drive system detector 380 can continue to monitor the status of the drive system 300 by querying the output from the voltage signal applied across the conductive element at regular intervals.

In the "drop-detected" mode—where the controller device 200 is coupled together with the pump device 100, but the conductive element coupled to the drive system 300 is broken—a voltage applied across the conductive element will indicate a "high" signal (e.g., measurably larger than the aforementioned ground or "low" signal). The "high" signal can be detected by the software component of the drive system detector 380, and in response thereto, the control circuitry 240 in controller device 200 will operate the pump system 10 is in the "drop-detected" mode. As described in more detail below, when the "drop-detected" mode is activated, the controller device 200 can initiate appropriate user safety countermeasures for the pump system 10.

In the "disconnected" mode (e.g., where the controller device 200 is not coupled with the pump device 100 at connectors 118 and 218), the drive system detector 380 can provide an alert to the user even if the pump device 100 suffered damage while separated from the controller device 200. In such circumstances, the drive system detector 380 passively detects the possible damage or inoperability of the drive system (e.g., because the conductive element of the drive system detector 380 is broken), which thereby enables the controller device 200 to alert the user prior to attempting to dispense medicine from the pump device 100. For example, in response the damaged pump device 100 being connected to the controller device 200, the software component of the drive system detector 380 (or a different component of the control circuitry 240) may cause a voltage to be applied across the conductive element. If the conductive element is broken (e.g., due to a break in the drive rod 370 or another component of the drive system 300), the drive system detector 380 will detect a "high" signal (e.g., measurably larger than the aforementioned ground or "low" signal). In response thereto, the control circuitry 240 will alert the user and initiate appropriate user safety countermeasures for the pump system 10 prior to dispensing medicine from the pump device 100.

Figure 12:
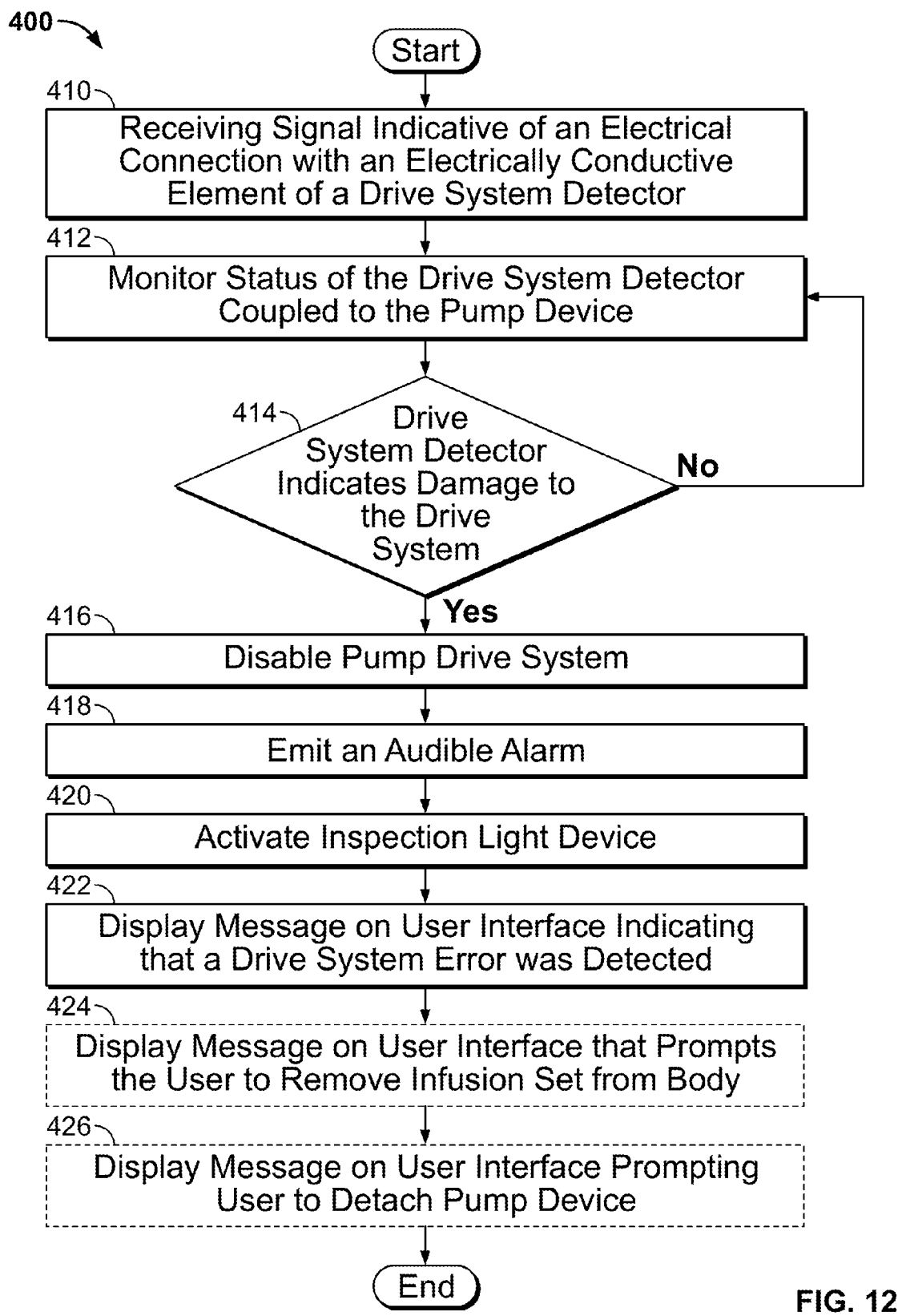
FIG. 12 is a flowchart describing a process of using a drive system detector of an infusion pump system, in accordance with some embodiments.

Referring now to FIG. 12, a controller of an infusion pump system can implement a process 400 of detecting damage to the drive system 300 (FIG. 7) using a drive system detector of the infusion pump system. Such a process 400, for example, can be implemented by the controller device 200 of the pump system 10 (FIG. 1). Alternatively, some operations of the process 400 could be implemented in an infusion pump system in which the controller and the pump drive system are integrated into a single housing.

In operation 410, the controller device can receive an electrical signal indicating that an electrical connection with an electrically conductive element of a drive system detector. For example, in the embodiments in which controller device 200 is separately housing from the pump device 100, the two components can be electrically connected via the connectors 118 and 218. As such, the controller device 200 can be electrically connected to an electrically conductive element of the drive system detector (e.g., the one or more conductive strips or wires coupled to the piston rod, an electrically conductive material of the piston rod, or the like), and the signal can indicative of the voltage across the flexible piston rod 370 as described above in reference to FIGS. 7-11.

In operation 412, the controller device monitors the status of the drive system detector. Such a monitoring operation can include periodic samplings of a voltage value indicating the voltage or electrical impedance measured across the flexible piston rod 370 (FIG. 7). For example, if the drive system detector 380 indicates that the pump system 10 is in a "normal" mode of operation, the monitoring operation 412 would reveal a signal (e.g., corresponding to a voltage or electrical impedance value) that is different (e.g., where the voltage value or electrical impedance is substantially zero or ground) from the signal when in the "drive system error" mode. That is, in some embodiments described above, a "drive system error" mode may be signaled when the drive system 300 is in a mode of operation whereby the voltage value or electrical impedance measured of the flexible piston rod 370 is substantially greater than ground.

In operation 414, the controller device determines if the drive system detector indicates damage to the drive system. For example, in the embodiments shown in FIGS. 7-11, the drive system detector 380 can indicate that damage to the flexible piston rod 370 occurred when a voltage value greater than zero (e.g., not ground) is detected by a software component of the drive detector 380 (and thereby indicating a "drive system error" mode). If the drive detector does not indicate that damage to the drive system 300 has occurred, the process 400 returns to the monitoring operation 412. If the "drive system error" mode is signaled a time after the pump device 100 is connected to the controller device 200 (e.g., the pump device 100 experienced a significant impact when attached to the controller device 200), the monitoring operation 412 would indicate damage to the drive system based on a measurement of a voltage value corresponding to electrical current applied across the flexible piston rod 370. If the "drive system error" mode is signaled immediately upon connect of the pump device 100 to the controller device 200 (e.g., the pump device 100 experienced a significant impact when separated from the controller device 200), the repeated cycle of monitoring damage sustained to the drive system could be bypassed.

Still referring to FIG. 12, if the drive detector indicates damage to the drive system, the controller device can respond according to some or all of the operations 416, 418, 420, 422, 424, and 426. In operation 416, in response to the controller device's determination that the drive detector system indicates the drive system 300 has sustained damage or is otherwise inoperable, the controller device can act to disable the pump drive system. For purposes of safety, the pump system 10 may immediately stop the delivery of medicine to the user of the system. As described above, the cessation of medicine delivery can be an appropriate user safety precaution because damage to the drive system 300 may cause an over-dosage or under-dosage could occur of medicine, depending on particular circumstances. As an alternative to automatically disabling the pump drive system, the process 400 can instead include an operation in which the user is prompted to confirm/approve that the pump drive system can be disabled. In addition to (or in as an alternative to) disabling the pump drive system, the controller device can initiate further user safety countermeasures as described in the next steps of operation process 400.

In operation 418, the controller device can emit an audible alarm in response to a determination of damage to the drive system (e.g., drive system 300). The purpose of the audible alarm is to alert the user to the issue that the pump system 10 is not operating normally and requires attention. The audible alarm can be emitted before, after, or simultaneously with the operation 416 of disabling the drive system.

Optionally, in operation 420, a separate light device of the pump system can be activated to provide a visible alarm (in addition to the audible alarm of operation 418). For example, the inspection light device 230 of pump system 10 can be activated to provide a visual notification to the user to the issue that the pump system 10 is not operating normally and requires attention.

In operation 422, the controller device can display a message to indicate that a drop event was detected in response to a determination of an impact at or above the threshold level. For example, the user interface display screen 222 on the controller device 200 can display a short textual message to alert the user (e.g., "Drive System Error"). The message can provide the user with an explanation of the reason for the audible and visual alarms. Further, the message can provide the user with an explanation that the pump drive system was automatically disabled.

Optionally, in operation 424, the controller device can display a message prompting the user to remove the infusion set from the user's body. For example, the user interface display screen 222 on the controller device 200 can display the message prompting the user to remove the infusion set from the user's body. This message can be provided in order to assist the user with taking the proper actions to prevent an over dispensation of medicine to the user's body as a result of the detected impact.

Optionally, in operation 426, the controller device can display a message prompting the user to detach the pump device from the controller device. For example, the user interface display screen 222 on the controller device 200 can display a message prompting the user to detach the pump device 100 from the controller device 200. In order to resume use of the pump system 10, the pump device 100 that sustained damage to the drive system 300 will need to be removed from the controller device 200 so that a new pump device, such as pump device 100' (refer to FIGS. 4 and 5) can be coupled with the controller device 200. This message assists the user to take the proper actions in response to damage detected by the drive system detector, and to proceed towards resumption of the use of a properly functioning pump system 10.

Figure 13:
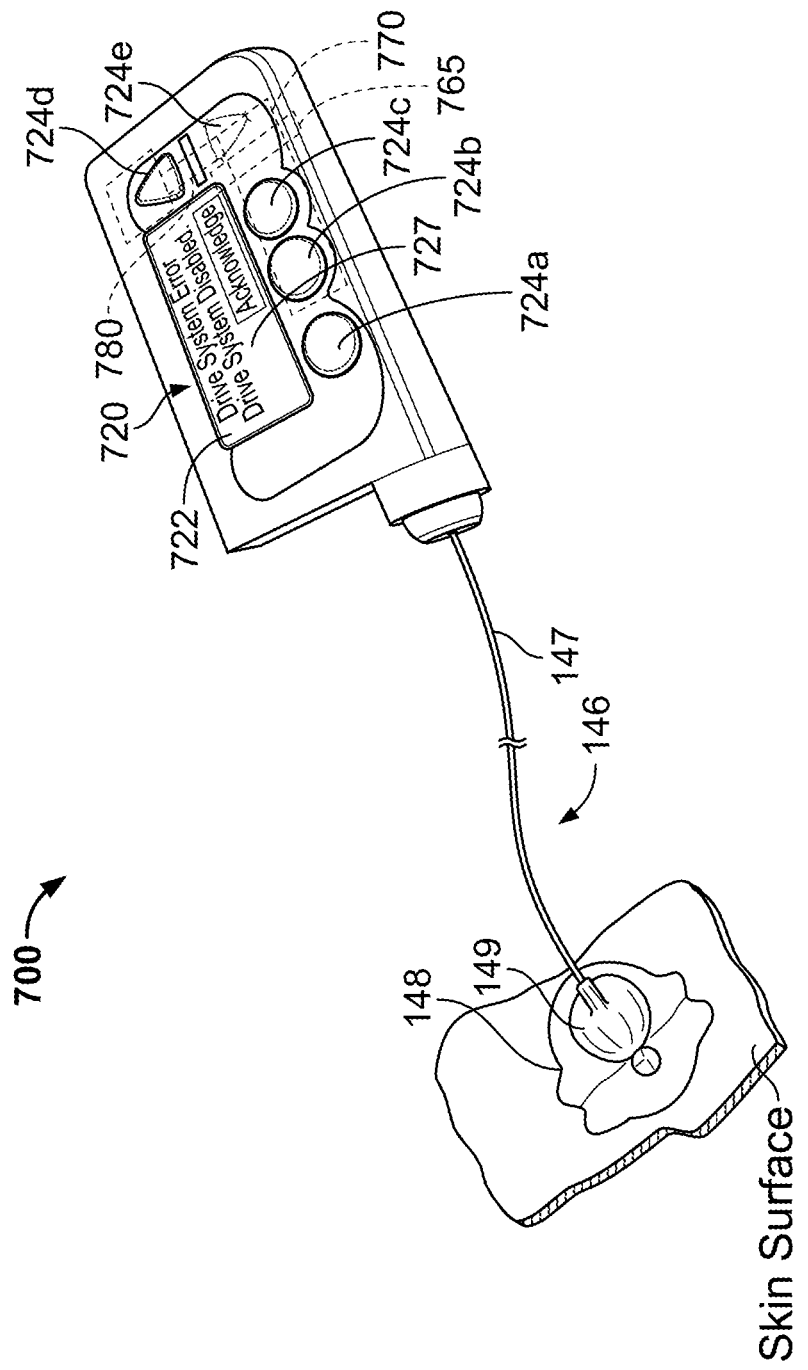
FIG. 13 is a perspective view of an alternative infusion pump system that includes a drive system detector, in accordance with some embodiments.

Referring now to FIG. 13, some embodiments of a portable infusion pump system 700 having a drive system detector 780 can employ a reusable pump apparatus (rather than a disposable pump device as previously described). In such circumstances, the infusion pump system 700 may comprise a reusable device that houses the control circuitry and the pump drive system within a single housing construct. In the particular embodiment depicted in FIG. 16, the pump system 700 comprises a reusable pump device that houses both the controller circuitry and the pump drive system (which may include a piston rod 370 and one or more gears 365). Similar to previously described embodiments, the pump system 700 can include a housing structure that defines a cavity in which a medicine cartridge can be received (not shown in FIG. 13; refer for example to cartridge 120 in FIG. 1). For example, the pump system 700 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 700 on the user's skin under clothing or in the user's pocket while receiving the medicine dispensed through the infusion set 146.

Similar to previously described embodiments, the infusion pump system 700 may include the drive system detector 780 that can detect damage to one or more components of the drive system (e.g., one or more of the piston rod 770 and the gears 765). Similar to previously described embodiments, the drive system detector 780 may include one or more conductive elements mounted to respective components of the drive system, and may also include a software component configured to query the one or more conductive elements. The occurrence of damage the drive system (e.g., damage to the piston rod 370, damage or non-alignment of one or more gears 365, or the like) may cause the infusion pump system 700 to potentially malfunction or otherwise cause over-dosage or under-dosage of medicine to the user. Such damage may occur, for example, when the pump system 700 is exposed to an impact force, for example, by dropping the infusion pump system 700 onto a floor or other hard surface, and by subjecting the infusion pump system 700 other types of impacts.

Figure 11:
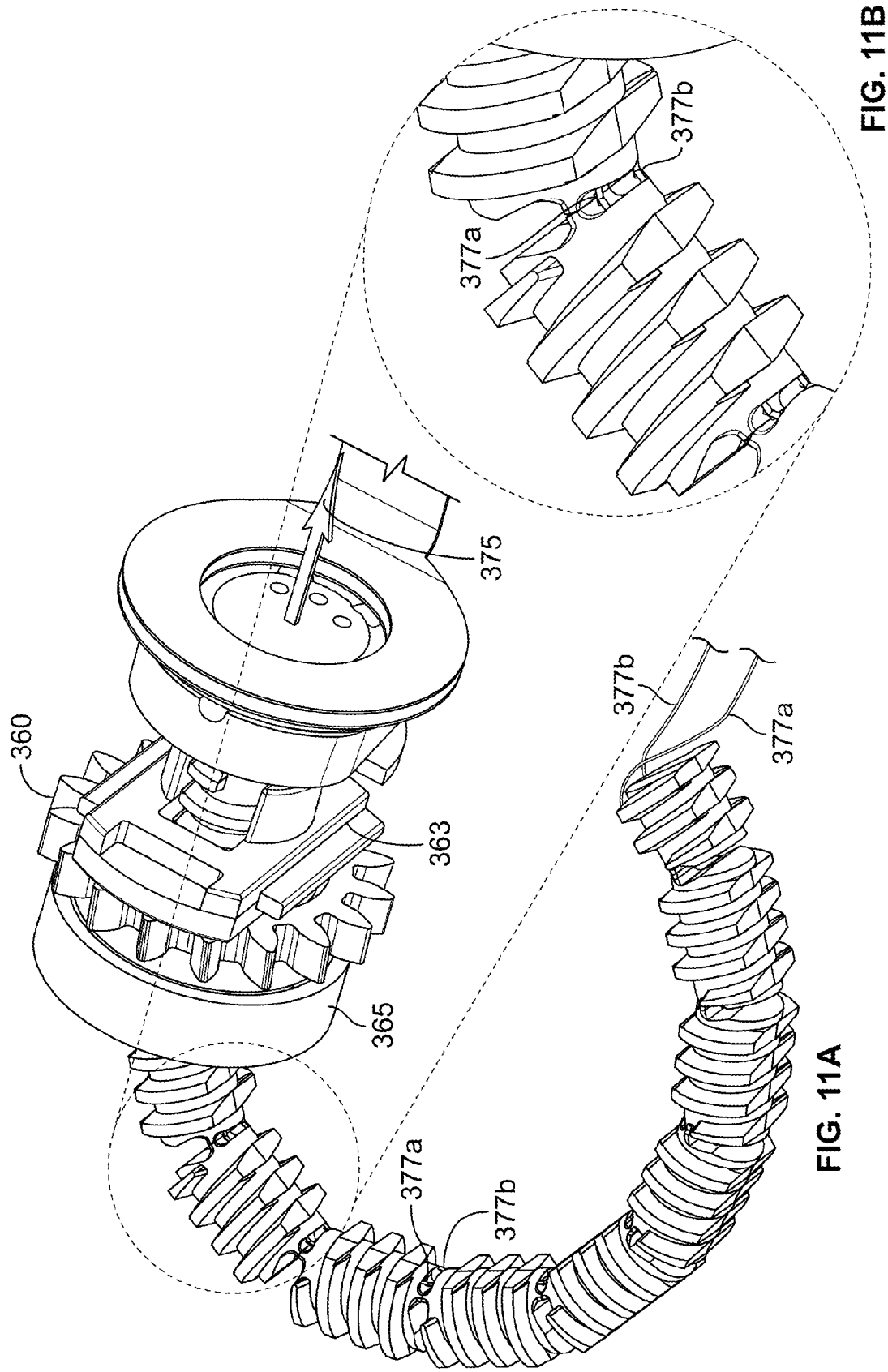
FIGS. 11A-B are perspective views of a portion of an alternative drive system detector for use in the pump device of FIG. 7, in accordance with some embodiments.

Accordingly, the drive system detector 780 of the infusion pump system 700 can operate similarly to any of the embodiments described above, such as the conductive strip embodiments depicted in FIGS. 7-9, the external conductive wire embodiment depicted in FIG. 10, the internal conductive wire embodiment depicted in FIG. 11, or the embodiment in which a component of the drive system comprises a conductive material as described above.

In some embodiments, the electrical connections associated with the drive system detector for use with the mechanism 780 can be similar to the drive system detector electrical connections described in reference to FIGS. 7-11, but with a few adaptations. For example, because the infusion pump system 700 has a single housing, the drop detector circuit may not necessarily communicate via the electrical connectors 118 and 218. Consequently, the drive detector electrical connections used with the drive system detector 780 in the infusion pump system 700 may optionally be a simplified version of the drive system detector 380 depicted in FIG. 7.

Still referring to FIG. 13, the user interface 720 of the pump system 700 includes a display device 722 and one or more user-selectable buttons 724*a-e*. The display device 722 can include an active area in which numerals, text, symbols, images, or a combination thereof can be displayed (as shown, for example, in FIG. 13). For example, the display device 722 can be used to communicate to the user that a drop event has been detected and the drive system has been disabled (similar to the process described in reference to FIG. 12). Also, the display device 722 can be used to communicate a number of settings or menu options for the infusion pump system 700. For example, the display device 722 can be used to communicate medicinal delivery information 727, such as the basal delivery rate, a bolus dosage, a historical record of medicine delivered, the amount of medicine remaining in the cartridge, or the like. In another example, the display device 722 can be used to communicate time and date information, which can be used by the user to determine dosage schedules, bolus delivery times, meal times, or the like.

Accordingly, the user may press one or more of the buttons 724*a*, 724*b*, 724*c*, 724*d*, and 724*e* to shuffle through a number of menus or program screens that show particular settings and data (e.g., review data that shows the medicine dispensing rate, the total amount of medicine dispensed in a given time period, the amount of medicine scheduled to be dispensed at a particular time or date, the approximate amount of medicine remaining in the cartridge 120, or the like). Also, the user can adjust the settings or otherwise program the pump system 700 by pressing one or more buttons 724*a*, 724*b*, 724*c*, 724*d*, and 724*e* of the user interface 420. Thus, the user can contemporaneously monitor the operation of the pump system 700, including any messages pertaining to the drop detection system from the same user interface 720.

A number of embodiments of the invention have been described. Nevertheless, it will be understood that various modifications may be made without departing from the spirit and scope of the invention. Accordingly, other embodiments are within the scope of the following claims.

What is claimed is:

1. A portable infusion pump system, comprising:
a pump device including a pump housing that defines a space to receive a medicine, a drive system positioned in the pump housing to dispense the medicine from the pump device when the medicine is received in the space of the pump housing, wherein the pump housing houses at least one electrically conductive element of a drive system detector that is mounted to a component of the drive system;
a controller device removably attachable to the pump housing so as to electrically connect with the pump device, wherein the controller device houses control circuitry configured to communicate with the drive system positioned in the pump housing to control dispensation of the medicine from the pump device,
wherein the control circuitry of the controller device is configured to disable the drive system in response to the drive system detector indicating damage to one or more components of the drive system,
wherein the electrically conductive element of the drive system detector is mounted to a piston rod of the drive system and is in electrical communication with the control circuitry that includes computer-readable instructions stored on a computer-readable medium housed in the controller device that, when executed by a processor of the control circuitry, measures an electrical characteristic of the electrically conductive element mounted to the piston rod, and wherein the drive system detector shifts indicates damage to one or more components of the drive system when the electrical characteristic is substantially greater than zero.

2. The portable infusion pump system of claim 1, wherein at least the electrically conductive element of the drive system detector is housed in the pump housing and at least a software component of the drive system detector is stored in a memory device housed in the controller device.

3. The portable infusion pump system of claim 1, wherein at least the electrically conductive element of the drive system detector is in electrical communication with the control circuitry housed in the controller device so that the control circuitry initiates an alarm when the drive system detector indicates damage to one or more components of the drive system.

4. The portable infusion pump system of claim 1, wherein, in response to the drive system detector indicating damage to one or more components of the drive system, the control circuitry is configured to disable the drive system, activate an audible alarm, and display one or more messages on a user interface display located on the controller device.

5. The portable infusion pump system of claim 1, wherein the electrically conductive element mounted to the piston rod includes at least one of (i) an electrically conductive strip applied to the surface of the piston rod, (ii) an electrically conductive wire attached to the surface of the piston rod, and (iii) an electrically conductive wire embedded into the piston rod.

6. The portable infusion pump system of claim 1, wherein the electrically conductive element comprises a conductive paint strip applied to a surface of a piston rod of the drive system and arranged in two substantially parallel lines that connect at a loop back proximate to a leading end of the piston rod to form a continuous U-shaped electrical path.

7. The portable infusion pump system of claim 1, wherein the electrically conductive element comprises a conductive wire attached to a surface of a piston rod of the drive system, wherein first and second portions of the conductive wire are substantially parallel with respective to each other and join together an electrically conductive loopback path proximate to a leading end of the piston rod to form a continuous U-shaped electrical path.

8. The portable infusion pump system of claim 1, wherein the electrically conductive element comprises a conductive wire embedded into a piston rod of the drive system, wherein first and second portions of the conductive wires are substantially parallel with respect to each other and join together at an electrically conductive loopback path proximate to a leading end of the piston rod form a continuous U-shaped electrical path.

9. The portable infusion pump system of claim 1, wherein the pump device is a one-time-use device equipped with one or more structures configured to prevent reuse of the pump device, wherein the pump housing includes an interior wall that defines a space to slidably receives an outer wall of a pre-filled medicine cartridge insertable through an opening defined by the pump housing, wherein the pump device further comprises a cap device that directly engages with the pump housing to enclose the pre-filled medicine cartridge in the pump housing when the pre-filled medicine cartridge is received in the space of the pump housing, and wherein the controller device is a reusable controller device including: a controller housing that is removably attachable to the pump housing in a fixed relationship; one or more electrical contacts disposed on the controller housing, the electrical contacts of the controller device being engageable with corresponding electrical contacts of the pump device when removably attached.

10. The portable infusion pump system of claim 1, wherein the pump device is a one-time-use device equipped with one or more structures configured to prevent reuse of the pump device.

11. A portable infusion pump system, comprising:
a pump device including a pump housing that defines a space to receive a medicine, a drive system positioned in the pump housing to dispense the medicine from the pump device when the medicine is received in the space of the pump housing, wherein the pump housing houses at least one electrically conductive element of a drive system detector that is mounted to a component of the drive system;
a controller device removably attachable to the pump housing so as to electrically connect with the pump device, wherein the controller device houses control circuitry configured to communicate with the drive system positioned in the pump housing to control dispensation of the medicine from the pump device,
wherein the control circuitry of the controller device is configured to disable the pump drive system in response to the drive system detector indicating damage to one or more components of the drive system, and further wherein the controller device is configured to monitor when the drive system has sustained an impact and is configured to initiate one or more user safety countermeasures upon detection that the drive system has sustained the impact.

12. The portable infusion pump system of claim 11, wherein the controller device includes at least computer-readable instructions stored on a computer-readable medium housed in the controller device that, when executed by a processor of the control circuitry, measures an electrical characteristic of the electrically conductive element mounted to the piston rod.

13. The portable infusion pump system of claim 12, wherein the drive system detector indicates damage to one or more components of the drive system when the electrical characteristic is substantially greater than zero.

14. The portable infusion pump system of claim 12, wherein the controller device initiates the one or more of the user safety countermeasures, the control circuitry is configured to disable the drive system, activate an audible alarm, and display of one or more messages on a user interface display located on the controller device.

15. The portable infusion pump system of claim 12, wherein the electrically conductive element mounted to the piston rod includes at least one of (i) an electrically conductive strip applied to the surface of the piston rod, (ii) an electrically conductive wire attached to the surface of the piston rod, and (iii) an electrically conductive wire embedded into the piston rod.

16. The portable infusion pump system of claim 12, wherein the electrically conductive element comprises a conductive paint strip applied to a surface of a piston rod of the drive system and arranged in two substantially parallel lines that connect at a loop back proximate to a leading end of the piston rod to form a continuous U-shaped electrical path.

17. A portable infusion pump system, comprising:
a space to receive a medicine;
a drive system to dispense the medicine when the medicine is received in the space;
at least one electrically conductive element of a drive system detector that is mounted to a component of the drive system; and
control circuitry configured to communicate with the drive system to control dispensation of the medicine;
wherein the control circuitry is configured to disable the drive system in response to the drive system detector indicating damage to one or more components of the drive system;
wherein the electrically conductive element of the drive system detector is mounted to a piston rod of the drive system and is in electrical communication with the control circuitry that includes computer-readable instructions stored on a computer-readable medium that, when executed by a processor of the control circuitry, measures an electrical characteristic of the electrically conductive element mounted to the piston rod, and wherein the drive system detector indicates damage to one or more components of the drive system when the electrical characteristic is substantially greater than zero.

18. The portable infusion pump system of claim 17, wherein the electrically conductive element mounted to the piston rod includes at least one of (i) an electrically conductive strip applied to the surface of the piston rod, (ii) an electrically conductive wire attached to the surface of the piston rod, and (iii) an electrically conductive wire embedded into the piston rod.

19. The portable infusion pump system of claim 17, wherein the drive system is equipped with one or more structures configured to prevent reuse of the pump device.

20. The portable infusion pump system of claim 17, wherein, in response to the drive system detector indicating damage to one or more components the drive system, the control circuitry is configured to disable the drive system, activate an audible alarm, and display of one or more messages on a user interface display.

* * * * *